(12) United States Patent
Slaby et al.

(10) Patent No.: US 11,433,178 B2
(45) Date of Patent: Sep. 6, 2022

(54) INFUSION PUMP ALIGNMENT FEATURES FOR VERTICALLY-ORIENTATED IV TUBES

(71) Applicants: BAXTER INTERNATIONAL INC., Deerfield, IL (US); BAXTER HEALTHCARE SA, Glattpark (CH)

(72) Inventors: Jiri Slaby, Buffalo Grove, IL (US); Steve Pippin, Libertyville, IL (US); Kevin Boron, Chicago, IL (US); Robert Cuevas, Twin Lakes, WI (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 78 days.

(21) Appl. No.: 16/869,869

(22) Filed: May 8, 2020

(65) Prior Publication Data

US 2020/0353157 A1 Nov. 12, 2020

Related U.S. Application Data

(60) Provisional application No. 62/845,435, filed on May 9, 2019.

(51) Int. Cl.
*A61M 5/142* (2006.01)

(52) U.S. Cl.
CPC ... *A61M 5/142* (2013.01); *A61M 2005/14208* (2013.01); *A61M 2205/0216* (2013.01)

(58) Field of Classification Search
CPC .......... A61M 2005/14208; A61M 2205/0216; A61M 5/142; A61M 2206/20; A61M 39/28; A61M 5/14212; A61M 5/16831; A61M 5/14; A61M 39/00; A61M 5/168
See application file for complete search history.

(56) References Cited

U.S. PATENT DOCUMENTS

2018/0187782 A1* 7/2018 Slaby ..................... F16J 15/104

* cited by examiner

*Primary Examiner* — Jason E Flick
(74) *Attorney, Agent, or Firm* — K&L Gates LLP

(57) ABSTRACT

Infusion pump alignment features for vertically-oriented IV tubes are disclosed. In an example, an infusion pump housing includes a tube channel having a radial curvature for bending an IV tube from a horizontal orientation to a vertical orientation when the infusion pump is positioned for operation. The housing also includes a hood having a first side and a second side that are divided by the tube channel. The infusion pump has a door that is connected to the housing for enclosing the tube channel and the hood. The door includes a cavity having dimensions to receive the hood when the door is in a closed position. The hood is configured to engage the cavity to prevent the door from closing if the IV tube is not positioned along the tube channel.

19 Claims, 26 Drawing Sheets

US 11,433,178 B2

INFUSION PUMP ALIGNMENT FEATURES FOR VERTICALLY-ORIENTATED IV TUBES

PRIORITY CLAIM

This application claims priority to and the benefit as a non-provisional application of U.S. Provisional Patent Application No. 62/845,435, filed May 9, 2019, the entire contents of which are hereby incorporated by reference and relied upon.

BACKGROUND

Infusion pumps, including large volume pumps ("LVP's") are designed to move fluid through an intravenous ("IV") line from a fluid supply to a patient. The infusion pumps move the fluid through the IV line with one or more actuator that applies a force to a portion of the line. The rate at which a fluid is moved is based on a frequency at which the force is applied to the IV line. It is common for infusion pumps to use a door or similar mechanism to secure a portion of the IV line for contact with the actuators. Other known pumps require the use of specialized IV line sets that are integrated with tube-carrying cassettes or over-molds that are mated with pump actuators.

An issue with known infusion pumps is that an IV tube is usually obscured from view after it is loaded and a door is closed. While the door is being closed, the IV tube may become misaligned, crimped, folded, or compressed, thereby obstructing medication flow to a patient. The misalignment may result from slack in the IV tube or a portion of the door pulling or pressing on a section of the IV tube as the door is closed. In some instances, the misalignment may cause an IV tube to crack or form a hole, which enables medication to leak into the pumping mechanism and/or electronics of the infusion pump. An operator may not become aware of a misalignment until after an infusion therapy is started, which could place a patient at risk.

SUMMARY

The present disclosure describes an infusion pump configured to deliver intravenous ("IV") fluids to a desired source, such as a human or animal (e.g., patient). The infusion pump includes guides, interlocking or meshed ribs or plates, retention knobs, and/or rails that are configured to provide and retain an IV tube within an IV tube channel that is defined within an infusion pump. The disclosed guides, interlocking ribs or plates, retention knobs, and/or rails may be located on a front case, exterior-side of a door, and/or interior-side of a door. During operation, the disclosed guides, interlocking ribs or plates, retention knobs, and/or rails are configured to move or direct an IV tube to a defined position within an IV tube channel during a self-positioning process. The interlocking ribs/plates are configured to prevent door closure if the IV tube is misaligned, such as when the guides, retention knobs, and rails have not retained the IV tube.

The example configurations disclosed herein are operable with conventional IV tubes. As a result, specialized IV tubes, receptacles, cartridges, or additional parts are not needed. Materials for the different components of the infusion pumps discussed below may include metal, plastic, rubber and combinations thereof that enable prolonged use without material deformation.

Aspects of the subject matter described herein may be useful alone or in combination with one or more other aspect described herein. Without limiting the foregoing description, in a first aspect of the present disclosure, an infusion pump for delivering an intravenous ("IV") fluid includes an actuation area configured to engage a first portion of an IV tube in a vertical orientation when the infusion pump is positioned for operation. The actuation area includes a top end for receiving the IV tube from a fluid container and a bottom end for providing the IV tube to a patient. The housing also includes a tube channel located at the top end of the actuation area. The tube channel has a surface curvature and a width to accept a bottom side of a second portion of the IV tube. At least a portion of the tube channel has a radial curvature for bending the IV tube from a horizontal orientation to a vertical orientation when the infusion pump is positioned for operation. The housing further includes two parallel hood rails provided on either side of the tube channel, the hood rails having widths that extend outwardly from the tube channel. The housing additionally includes a hood having a first side and a second side that are divided by the hood rails, the first and second sides connected respectively to the hood rails and having widths equal to or less than the widths of the hood rails. The example infusion pump also includes a door connected to the housing and configured to enclose the actuation area, the tube channel, the hood rails, and the hood of the housing. The door includes a cavity having dimensions sized to receive the hood rails and the hood when the door is in a closed position. The hood and the hood rails are configured to engage the cavity to prevent the door from closing if the second portion of the IV tube is not positioned between the hood rails along the tube channel.

In accordance with a second aspect of the present disclosure, which may be used in combination with any other aspect listed herein unless stated otherwise, each of the hood rails includes a retention knob configured to retain the second portion of the IV tube within the tube channel.

In accordance with a third aspect of the present disclosure, which may be used in combination with any other aspect listed herein unless stated otherwise, the first side of the hood includes a cutout that is located on an opposite end from an end that is connected to the respective hood rail, the cutout reducing a width of the first side of the hood at the location of the cutout. The first side of the hood and the cutout cooperate to cause a misaligned second portion of the IV tube to move further away from the tube channel to exaggerate the misalignment.

In accordance with a fourth aspect of the present disclosure, which may be used in combination with any other aspect listed herein unless stated otherwise, the cavity includes a tab that is configured to fit within the cutout of the first side of the hood.

In accordance with a fifth aspect of the present disclosure, which may be used in combination with any other aspect listed herein unless stated otherwise, the cavity of the door is defined by an upper-pre-alignment guide that is configured to contact or be adjacent to a top face of the hood, and a lower pre-alignment guide that is configured to contact or be adjacent to a bottom face of the hood.

In accordance with a sixth aspect of the present disclosure, which may be used in combination with any other aspect listed herein unless stated otherwise, the upper pre-alignment guide includes channels configured to engage with or receive the respective hood rails.

In accordance with a seventh aspect of the present disclosure, which may be used in combination with any other aspect listed herein unless stated otherwise, the housing further includes under-hood rails that are positioned adjacent to the respective hood rails and located on each side of the tube channel, and guide ribs that are positioned a distance away from the respective under-hood rails and located on each side of the tube channel for retaining the second portion of the IV tube, wherein the distance between the under-hood rails and the guide ribs forms gaps.

In accordance with an eighth aspect of the present disclosure, which may be used in combination with any other aspect listed herein unless stated otherwise, the lower-pre-alignment guide includes cutouts that are configured to respectively receive the under-hood rails, and a guide section that is configured to be received in the gaps formed between the under-hood rails and the guide ribs, wherein a bottom face of the lower-pre-alignment guide is configured to contact or be adjacent to the guide ribs.

In accordance with a ninth aspect of the present disclosure, which may be used in combination with any other aspect listed herein unless stated otherwise, the under-hood rails, the gaps, and the guide ribs are configured to interlock or overlap with the lower-pre-alignment guide to prevent the door from closing if the second portion of the IV tube is not positioned between along the tube channel.

In accordance with a tenth aspect of the present disclosure, which may be used in combination with any other aspect listed herein unless stated otherwise, the guide section has at least one of a u-shape or a v-shape.

In accordance with an eleventh aspect of the present disclosure, which may be used in combination with any other aspect listed herein unless stated otherwise, the door further includes a pusher aligned with or adjacent to the tube channel when the door is in the closed position, the pusher having a surface curvature and a width to accept a top side of the second portion of the IV tube, at least a portion of the pusher having a radial curvature for bending the IV tube from the horizontal orientation to the vertical orientation when the infusion pump is positioned for operation, wherein the width of the pusher enables the pusher to fit between the parallel hood rails when the door is in the closed position.

In accordance with a twelfth aspect of the present disclosure, which may be used in combination with any other aspect listed herein unless stated otherwise, the housing further includes a seal section located along at least the top side of the housing. The seal section includes at least one rib positioned along the top side of the housing, the at least one rib extending vertically from the top side and defining a tube window having a width to enable the second portion of the IV tube to pass between edges of the tube window, and a rib tube channel aligned with the tube window. The rib tube channel has a horizontal orientation when the infusion pump is positioned for operation. The rib tube channel is located adjacent to the tube channel and is configured to contact the bottom side of the second portion of the IV tube.

In accordance with a thirteenth aspect of the present disclosure, which may be used in combination with any other aspect listed herein unless stated otherwise, the pusher in connection with the tube channel and the rib tube channel encloses or surrounds the bottom and top sides of the second portion of the IV tube and provides for bending the second portion of IV tube from the horizontal orientation to the vertical orientation.

In accordance with a fourteenth aspect of the present disclosure, which may be used in combination with any other aspect listed herein unless stated otherwise, the housing further comprises a clip at an end of the tube channel configured to receive the second portion of the IV tube.

In accordance with a fifteenth aspect of the present disclosure, which may be used in combination with any other aspect listed herein unless stated otherwise, an infusion pump apparatus for delivering an intravenous ("IV") fluid comprises a housing and a door. The housing includes an actuation area configured to engage a first portion of an IV tube in a vertical orientation when the infusion pump is positioned for operation, the actuation area including a top end for receiving the IV tube from a fluid container and a bottom end for providing the IV tube to a patient. The housing also includes a housing tube channel located at the top end of the actuation area, the housing tube channel having a surface curvature and a width to accept a bottom side of a second portion of the IV tube, at least a portion of the housing tube channel having a radial curvature for bending the IV tube from a horizontal orientation to a vertical orientation when the infusion pump is positioned for operation. The housing further includes a first set of housing ribs located on a first side of the housing tube channel and a second set of housing ribs located on a second, opposite side of the housing tube channel. The door is connected to the housing and configured to enclose the actuation area, the housing tube channel, and the housing ribs. The door includes a door tube channel that is configured to align with the housing tube channel when the door is in a closed position, and a first set of door ribs located on a first side of the door tube channel and a second set of door ribs located on a second, opposite side of the door tube channel. The first and second sets of housing ribs are configured to interlock or overlap with the first and second sets of door ribs when the door is in the closed position.

In accordance with a sixteenth aspect of the present disclosure, which may be used in combination with any other aspect listed herein unless stated otherwise, each of the first and second sets of housing ribs includes at least two parallel ribs and each of the first and second sets of door ribs includes at least two parallel ribs.

In accordance with a seventeenth aspect of the present disclosure, which may be used in combination with any other aspect listed herein unless stated otherwise, the housing tube channel, the door tube channel, the first and second sets of housing ribs, and first and second sets of door ribs include at least one of plastic, rubber, or combinations thereof.

In accordance with an eighteenth aspect of the present disclosure, which may be used in combination with any other aspect listed herein unless stated otherwise, the door further includes an upper pre-alignment guide that is configured to contact or be adjacent to a top rib of the first and second sets of housing ribs.

In accordance with a nineteenth aspect of the present disclosure, which may be used in combination with any other aspect listed herein unless stated otherwise, the door tube channel includes a pusher having a surface curvature and a width to accept a top side of the second portion of the IV tube, at least a portion of the pusher having a radial curvature for bending the IV tube from the horizontal orientation to the vertical orientation when the infusion pump is positioned for operation.

In accordance with a twentieth aspect of the present disclosure, which may be used in combination with any other aspect listed herein unless stated otherwise, the door further includes a roof configured to cover the top end of the actuation area, wherein the door tube channel, the first set of door ribs, and the second set of door ribs are located on the roof of the door.

In accordance with a twenty-first aspect of the present disclosure, any of the structure and functionality illustrated and described in connection with FIGS. 3 to 40 may be used in combination with any of the structure and functionality illustrated and described in connection with any of the other of FIGS. 3 to 40 and with any one or more of the preceding aspects.

In light of the aspects above and the disclosure herein, it is accordingly an advantage of the present disclosure to provide an infusion pump that ensures proper IV tube loading.

It is another advantage of the present disclosure to provide an infusion pump that prevents an IV tube from becoming misaligned, crimped, folded, or compressed when a door of the infusion pump is closed.

It is another advantage of the present disclosure to provide an infusion pump that prevents a door from being closed when the IV tube is misaligned.

It is a further advantage of the present disclosure to provide an infusion pump that may operate with standard, non-specialized pump sets and tubing.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
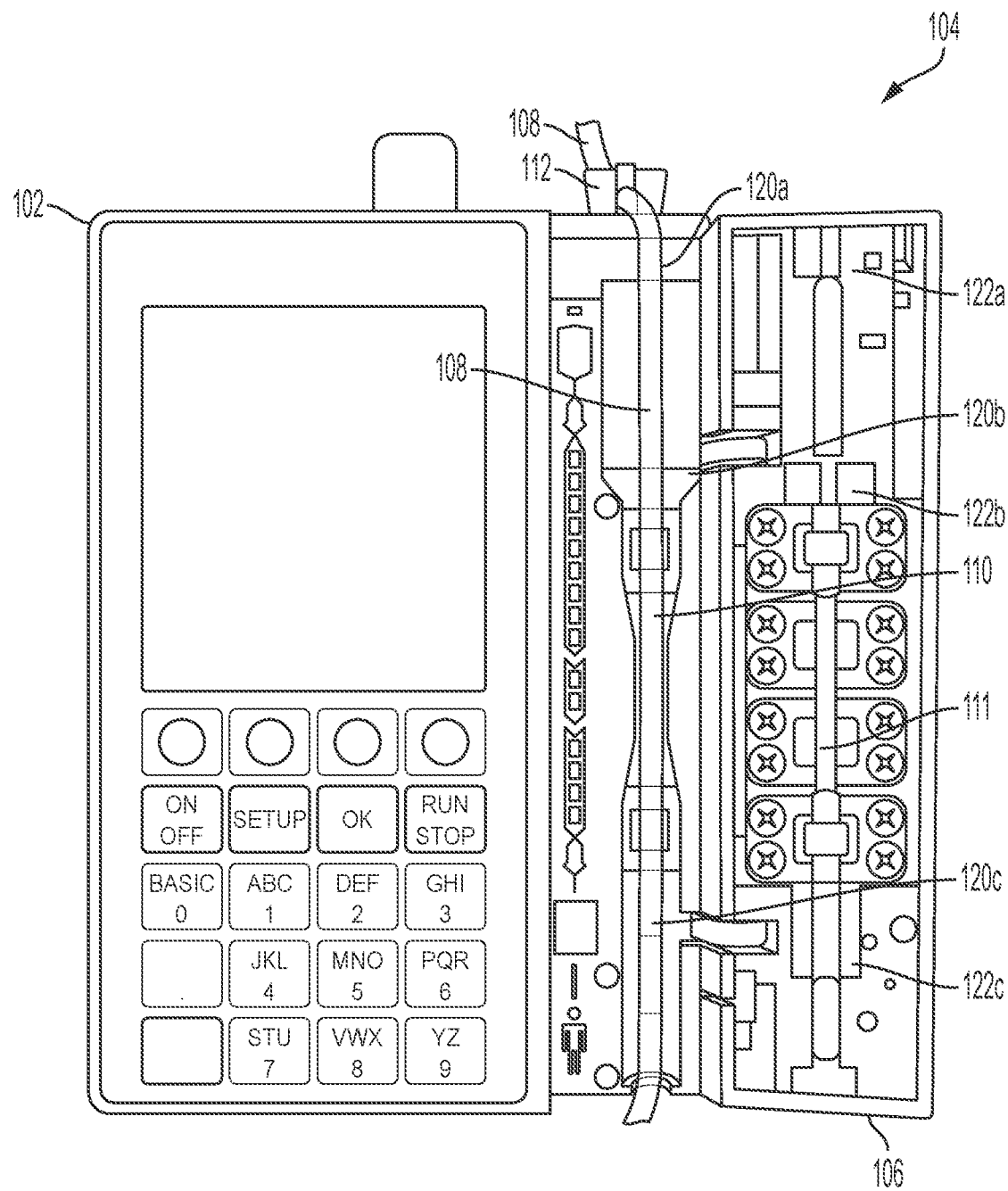
FIGS. 1 and 2 are diagrams of known infusion pumps that use different constructions to retain an IV tube.

The present disclosure relates in general to an infusion pump apparatus that includes features configured to secure at least a portion of an IV tube within a tube channel. The example disclosure describes self-alignment features of an infusion pump that prevent a door from closing when an IV tube is outside of a desired position. The example features disclosed herein are located inside of a door of an infusion pump. The door, when closed, typically obscures tube placement from a user's view. The self-alignment features described herein ensure that an IV tube does not become partially kinked, crimped, folded, compressed, or occluded, unbeknownst to a clinician. The self-alignment features include mechanical positioners configured to guide and secure an IV tube within a designed area. The automatic placement of the IV tube eliminates the need for costly electrical tube-placement sensors, which are prone to false alarms over time. The self-alignment features disclosed herein accordingly prevent patient medication delivery via an IV tube from becoming obstructed in a cost-efficient manner.

The example self-alignment features of the infusion pump disclosed herein may be located on a door, within an actuation area of an infusion pump, or a combination of both areas. The self-alignment features may include a hood fence, an under-hood rail, a gap and corresponding door V-guide, retention knobs, inner door rib guards, an upper pre-alignment guide, a lower pre-alignment guide, a tube pusher, and/or a door hood cavity. It should be appreciated that the example infusion pump may include all of the above features or at least a subset of the above features.

Reference is made throughout to infusion pumps that are configured to receive IV tubes in a vertical orientation (e.g., a first orientation). In other words, the infusion pumps receive an IV tube in a top section or side. However, it should be appreciated that in other embodiments the infusion pump self-alignment features disclosed herein may be provided to receive horizontally (or other desired angle) (e.g., a second orientation) orientated IV tubes. In the other embodiments, the IV tube enters a side of the infusion pump. In an embodiment, the infusion pump may be oriented in different positions for operation, such that the tube may be disposed differently for different procedures.

Likewise, the infusion pumps disclosed herein include general vertically orientated actuators for pumping fluid through the IV tubes. However, in other embodiments, the actuators may be positioned in a horizontal (or other desired angle) orientation. It should be appreciated that the orientation of the actuators may not necessarily correspond to the orientation of an IV tube entering the infusion pump. For example, an infusion pump may receive an IV tube in a horizontal orientation but have the actuators be aligned in a vertical orientation. Again, the actuators may be oriented differently for different procedures.

Reference is also made herein to minimal spacing between self-alignment features when a door of an infusion pump is in a closed position. The minimal spacing may be between 0.05 millimeters (mm) to 10 millimeters, preferably as small as possible permitting for manufacturing tolerance variations. Generally, the minimal spacing is less than a diameter of an IV tube, preferably less than a diameter of a fully compressed IV tube to prevent an infusion pump door from closing when the IV tube is kinked or otherwise misaligned.

Known Infusion Pumps

Figure 2:
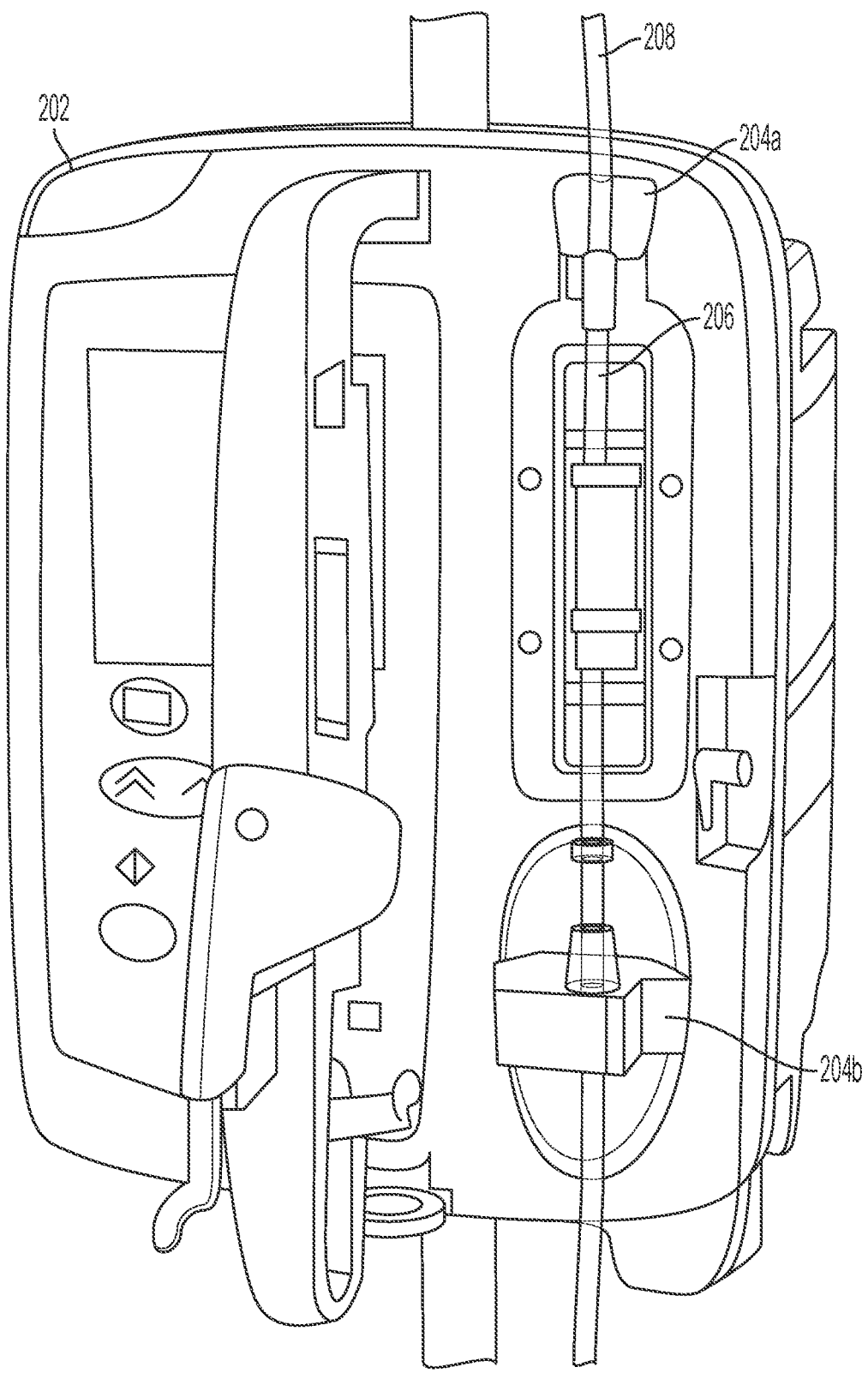

FIGS. 1 and 2 are diagrams of known infusion pumps that use different constructions to attempt to retain an IV tube within an actuation area. Specifically, FIG. 1 shows one infusion pump 102 that uses retainer clips or knobs to secure an IV tube. FIG. 2 shows another infusion pump that uses custom overmolds or cartridges to hold IV tubes.

The known infusion pump 102 of FIG. 1 includes an actuation area 104 enclosed by a door 106. An IV tube 108 is routed through the actuation area 104. In this illustration, actuators 110 are located within a main housing of the infusion pump. The actuators 110 are operable with spring loaded back-pushers 111 that are positioned on the door 106. The back-pushers 111 compensate for tolerance stack-up of components in the actuation area 104 and apply a constant force on the IV tube 108. Compression provided by the actuators 110 moves fluid through the IV tube 108. Closure of the door 106 causes the back-pushers 111 to contact or be in close proximity to a portion of the IV tube 108 within the actuation area 104. The actuators 110 are controlled to sequentially push against the IV tube 108 to move or pump a fluid through the tube 108 when the door 106 is closed.

The known infusion pump 102 is configured such that the IV tube 108 is orientated vertically through the actuation area 104. The IV tube 108 at its top end of the actuation area 104 is connected to a fluid container. The IV tube 108 at its bottom end of the actuation area 104 is connected to a patient. The infusion pump 102 includes a clip 112 or slide clamp that is configured to connect to the IV tube 108 at the top of the infusion pump 102. Insertion of the clip 112 into a slot causes the door 106 to open. Placement of the clip 112 in to the slot also causes the IV tube 108 to occlude to prevent fluid flow while the IV tube 108 is being loaded into the infusion pump 102. After the IV tube 108 is secured in the actuator area 104, the door 106 is closed and the clip 112 is removed, thereby enabling fluid to flow through the IV tube 108.

The known infusion pump 102 includes retainer clips 120a, 120b, and 120c that are configured to secure the IV tube 108 in place. The retainer clips 120 are located within the actuation area 104 and are obscured from view when the door 106 is closed. The retainer clips 120 do not prevent the IV tube 108 from kinking or bending. Instead, the clips 120 are configured to retain the IV tube 108 at only the location of contact. The IV tube 108 could become loose or misaligned during loading or when the door 106 is being closed. Further, in some instances, the back-pushers 111 may exert stress on the IV tube 108, causing it to be pulled out of place.

The example retainer clips 120a, 12b, and 120c are positioned to fit within corresponding channels 122a, 122b, and 122c on the door 106 when the door is moved to the closed position. The arrangement between the channels 122 and the clips 120 is designed to prevent the IV tube 108 from becoming displaced after the door 106 is closed. However, the arrangement between the channels 122 and clips 120 does not prevent an operator from misaligning the IV tube 108 during loading, and does not prevent the IV tube 108 from becoming misaligned while the door 106 is being closed. Further, the arrangement between channels 122 and clips 120 does not prevent crimping or bending of the IV tube 108.

FIG. 2 shows a diagram of another known infusion pump 202 that uses overmolds 204a and 204b and a cartridge 206 to secure an IV tube 208 in place. The overmold 204a and the cartridge 206 are integrated with the IV tube 208. In addition, the overmold 204b is configured to contact a portion of the IV tube 208 that has a wider diameter. While the combination of the overmolds 204 and the cartridge 206 secure the IV tube 208 in place, the components require the use of a customized IV tube. In many cases, the cost to customize the IV tube and produce the overmolds 204 and the cartridge 206 far exceed the cost of a standard IV tube. Such solutions are not desirable for cost reasons, which is especially significant in developing countries. Further, the overmolds 204 and cartridge 206 are unique to the associated pump 202. A change among pump models or design configuration may require a purchase of new corresponding IV tubes, rendering old tubes useless that are still in stock.

Still other known infusion pumps (not shown) have a tube opening along a side section. These known pumps have vertically orientated finger-shaped actuators. As one can appreciate, installation of the IV tube is complex since an operator has to bend the tube inside the actuation area along a defined channel. In addition, the use of the channel and horizontal orientation of the IV tube creates more opportunities for the IV tube to bend more than desired or crimp during installation. Further, the complex installation procedure creates more opportunities for an operator to misalign at least a portion of the IV tube, which may not be detected and cause an unwanted occlusion or tube leak.

Example Infusion Pump

Figure 3:
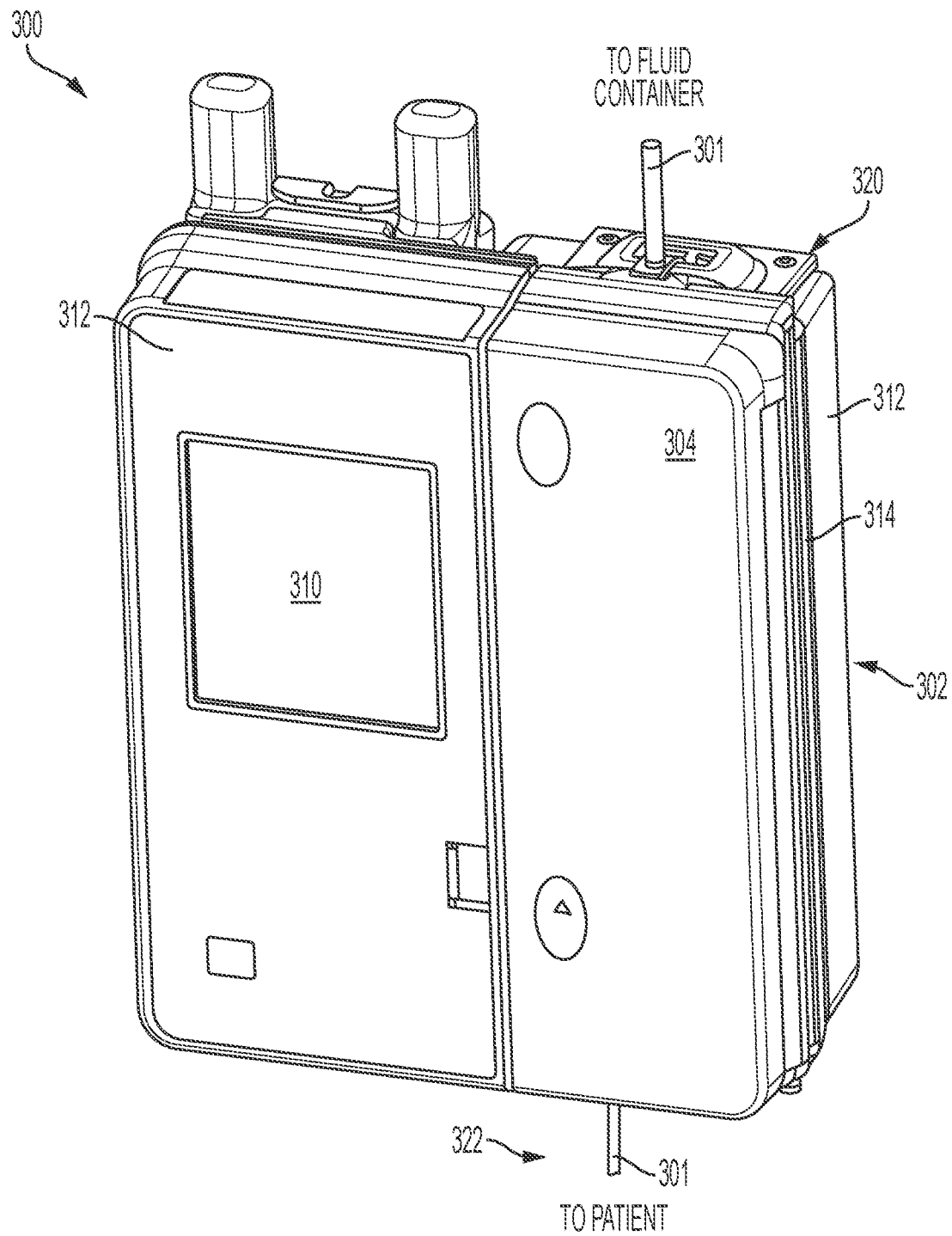
FIG. 3 is a diagram of an example infusion pump, according to an example embodiment of the present disclosure.

FIG. 3 is a diagram of an example infusion pump 300, according to an example embodiment of the present disclosure. The example infusion pump 300, as disclosed in more detail below, includes one or more self-alignment features including guides, interlocking ribs, retention knobs, and rails to ensure proper placement of an IV tube 301. The features are placed on a front case, outer door, and/or inner door within an actuation area 302 of the infusion pump 300. A first portion of the IV tube 301 is provided in the actuation area 302. A second, upstream portion of the IV tube 301 is provided at atop end 320 of the actuation area 302.

In some embodiments, the first portion of the IV tube in the actuation area 302 has a vertical orientation when the infusion pump 300 is positioned for operation. In some embodiments, the second portion of the IV at the top end 320 of the actuation area 302 is bent between a horizontal and a vertical orientation.

During operation, the self-alignment features cause at least a portion (the second portion) of an IV tube 301 to move into a desired position. In addition, at least some of the self-alignment features cause the IV tube 301 to be retained into place during placement by an operator or a closing of a door 304. Further, at least some of the self-alignment features prevent the door 304 from being closed if at least a portion of the IV tube is misaligned or out of position.

In an example embodiment, guides and rails cause at least a portion of the IV tube 301 to move into a desired position. Interlocking ribs are configured to prevent the door 304 from closing if at least a portion of the IV tube 301 is misaligned. Additionally, retention knobs are configured to hold at least a portion of the IV tube 301 in place for proper positioning opposite an IV tube positioning pusher during loading and door closure processes. The self-alignment features disclosed herein are operable with conventional IV tubes, so that specialized IV tubes, receptacles, cartridges, or additional parts are not needed.

The example infusion pump 300 may include any pump capable of delivering an intravenous therapy to a patient via one or more IV tubes or line sets. Examples include a linear peristaltic pump, a large volume pump ("LVP"), an ambulatory pump, and/or a multi-channel pump, etc. A linear peristaltic pump (such as the infusion pump 102 of FIG. 1) uses cams on a camshaft to compress part of a tube while the camshaft is rotating. Often, one or more fingers attached to the cams contact the tube for a certain period of rotation. The compressed rotation causes a defined amount of fluid to pass through the tube. LVP's typically use one or more finger or arm to compress a portion of intravenous therapy ("IV") tube. The timing of the finger actuation on the tube causes constant or near constant movement of a fluid through the tube.

The example infusion pump 300 of FIG. 3 includes a display interface 310 to display pump information, including a QR or barcode to convey a pump identifier or other infusion-related information. The display interface 310 may also facilitate the programming of the pump 300 via a touch screen, membrane switch, combinations thereof, or other type of user interface. The infusion pump 300, in an embodiment, also includes a housing 312 configured to enclose electronics and actuators, which are located within the actuation area 302. The infusion pump 300 further includes the door 304, which is shown in FIG. 3 in a closed position enclosing the actuation area 302. The example door 304 is configured (e.g., hinged) to open, thereby providing access to the actuation area 302. A clinician may open the door 304 to insert a portion of the IV tube 301 into the actuation area 302 by, for example, placing the IV tube into the above-described self-alignment features that hold the IV tube in place for actuation.

The example door 304 in the illustrated embodiment is connected to the housing 312 of the infusion pump 300 via one or more hinge 314. In the illustrated example, the hinges 314 are positioned on a side of the infusion pump 300, which causes the door 304 to swing away from the interface 310. Such a configuration enables a clinician to install the IV tube 301 while still being able to view the interface 310. Otherwise, locating hinges between the door 304 and interface 310 would cause the door 304 to open in the opposite direction, thereby obstructing the view of the interface 310. Materials for the different components of the infusion pump 300 discussed below may include metal, plastic, rubber and combinations thereof.

As illustrated in FIG. 3, the IV tube 301 enters (from a fluid flow standpoint) the infusion pump 300 at the top end 320 of the actuation area 302. The IV tube 301 at the top end 320 is connected to a fluid container, such as an IV bag. The IV tube 301 is generally orientated vertically above the top end 320 to enable gravity to pull fluid from the fluid container into the IV tube 301 and to allow air to collect at the top of a fluid container, such as an IV bag, thereby introducing IV fluid into the tube 301. The IV tube 301 exits (from a fluid flow standpoint) the infusion pump 300 at a bottom end 322 of the actuation area 304. The IV tube 301 at the bottom end 322 extends to its delivery destination, e.g., a patient.

In some embodiments, the example infusion pump 300 may include door seals and/or a door roof configured to enclose or protect an actuation area of an infusion pump from contaminants. The positioning of the seals with respect to the door is configured to isolate an actuation area independent of manufacturing tolerance variations of the overall door and/or pump casing. In an embodiment, a seal is formed at a door's edges, which relaxes the tolerance ranges of the pump housing and door, thereby reducing manufacturing costs. Disclosure of the door seals and door roof can be found in U.S. application Ser. Nos. 15/855,536 and 15/855,550, where are hereby incorporated by reference and relied upon.

Self-Alignment Features Embodiments

FIGS. 4 to 7 are diagrams that illustrate self-alignment features provided at the top end 320 of the housing 312 of the actuation area 302 of the infusion pump 300, according to example embodiments of the present disclosure. The self-alignment features include a hood 402 (shown as hood 402a and 402b) and a hood rail 403 that defines an opening or gap for an IV tube channel 404 (e.g., a tube channel 404 for the housing 312). The opening or gap defined by the hood rail 403 divides the hood 402 into two sides, including a first side 402a and a second side 402b. Each of the first and second sides 402a and 402b of the hood 402 have edges that connect to or are adjacent to the respective hood rail 403.

The example hood 402 includes a ledge or bar that extends in a horizontal direction when the infusion pump 300 is positioned for operation. The hood 402 is configured to have a width in the horizontal direction that extends from seal section 440 to enclose at least a portion of the IV tube 301 that is bent between horizontal and vertical orientations.

Figure 7:
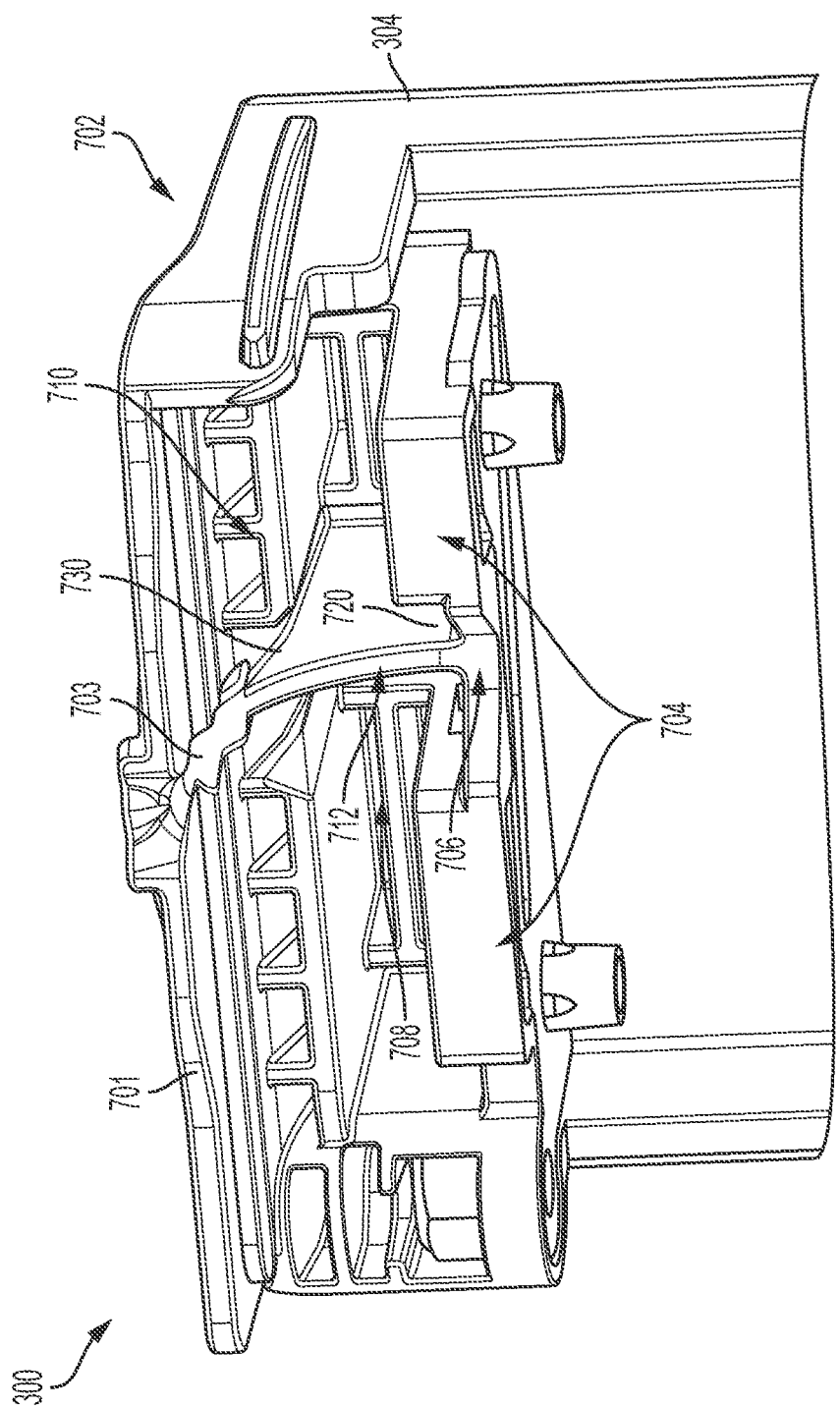

The hood 402 may include a cutout 410 that is dimensioned to enable closure of the door 304. The shape of the cutout 410 is configured to be flush against a hood cavity 708, as shown in FIG. 7. The flushness of the connection prevents the door 304 from closing if the IV tube 301 is placed between the hood 402 and the hood cavity 708. In the illustrated embodiment, the cutout 410 is dimensioned to have a width equal to a width of the hood rail 403, then decrease in width as the hood 402 approaches the hinge 314. This dimensioning of the hood 402 at the cutout 410 causes any slight misalignment of the IV tube 301 outside of the tube channel 404 to move further away from the tube channel 404 and into the cutout 410 area. This exaggerated misalignment is more visible to an operator, and is more likely to prevent the door 304 from closing.

In the illustrated embodiment, only the hood 402a includes the cutout 410. In other embodiments, the hood 402b may also include a cutout. Further, in other embodiments, the cutout 410 may have different shapes and/or dimensions. Alternatively, the hood 402a may not include the cutout 410.

The example hood rail 403 is configured to direct the IV tube 301 into the tube channel 404. In addition, the hood rail 403 (on each side of the tube channel 404) has a width that is at least greater than a width of the IV tube 301, which prevents the IV tube 301 from easily becoming displaced from the tube channel 404. In some instances, the hood rails 403 have a width that is appropriate to capture the IV tube 301 and guide it to its place in the tube channel 404. In some embodiments, the width of hood rail 403 (e.g., the outward extension from the actuation area 302) is at least 50% greater than a width or diameter of the IV tube 301.

In some embodiments, the example hood rail 403 is configured to have a height at a first end 430 that is flush with a seal section 440. In other embodiments, the hood rail 403 has a height at the first end 430 that is lower than a height of the seal section 440. The height of the hood rail 403 decreases in height to a second end 432, which may conform to self-alignment features on the door 304. In other embodiments, the height of the hood rail 403 is the same at the first end 430 and the second end 432.

Figure 4:
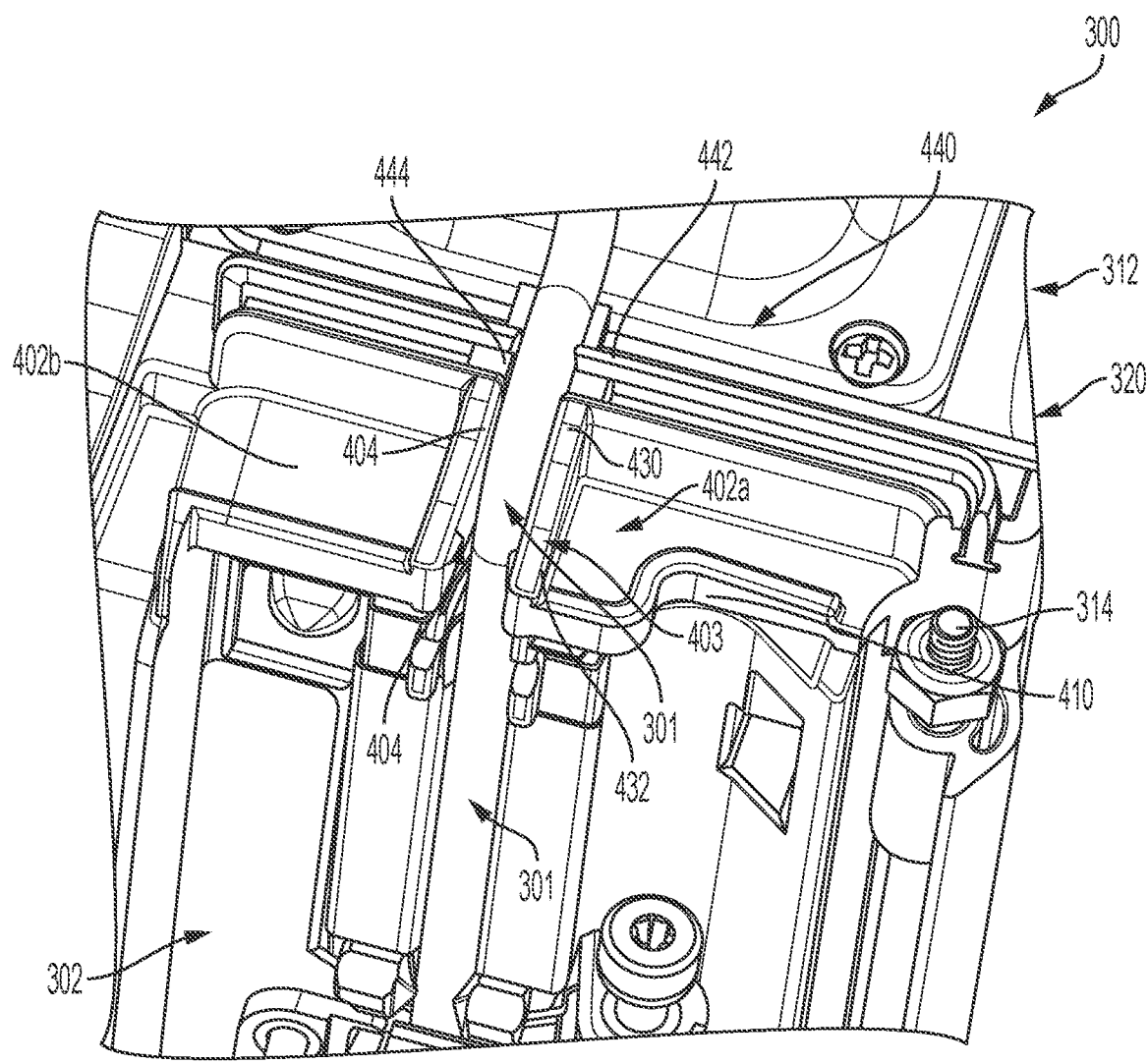
FIGS. 4 to 7 are diagrams that illustrate self-alignment features of the infusion pump of FIG. 3, according to example embodiments of the present disclosure.

As illustrated in FIG. 4, the example tube channel 404 has a radial curvature that enables or causes a portion of the IV tube 301 to be bend (without occluding) from a first orientation (e.g., a horizontal orientation) at the seal section 440 to a second orientation (e.g., a vertical orientation) within the actuation area 302. The hood rail 403 is configured to retain the bent IV tube 301 in place within the tube channel 404. The tube channel 404 also has a surface curvature and width for receiving the IV tube 301 and/or enclosing at least a bottom side of the IV tube 301.

The seal section 440 in an embodiment includes ridges configured to sandwich and/or support a gasket rib 442. The illustrated ridges extend vertically. In some instances, the ridges have the same heights and/or widths. In other instances, the ridges have varying heights and/or widths. For example, the gasket ridge 442 may include a lip or edge that extends further vertically than the other ridges.

The example gasket rib 442 is positioned to run along the seal section 440 between the ridges. In some instances, an end of the gasket rib may extend from the ridges, as shown in FIG. 4. The gasket rib 442 may include an elastomeric material to help create a seal against a roof when the door 304 is closed. The gasket rib 442 includes a tube window positioned at the top end 320 of the housing 312 adjacent to where the IV tube 301 is received into the actuation area 302. The tube window may be integrated with the gasket rib 442 such that both are made of the same material. In other instances, the tube window may be connected to the gasket rib 442. The tube window in the illustrated embodiment extends vertically above the gasket rib 442 such that edges of the tube window contact external sides of the IV tube 301. In some instances, the edges of the tube window may be curved to conform to a surface curvature of the IV tube 301 to provide a secure connection without compressing the IV tube 301.

The gasket rib 422 may also include a rib tube channel 444 that is located at the tube window. The rib tube channel 444 is configured to cradle, connect, or otherwise accept the IV tube 301. The rib tube channel 444 is adjacent to the tube channel 404 to provide a substantially continuous half-enclosure for the IV tube 301. The elastomeric nature of the tube window, the rib tube channel 444, and channel 404 enables the IV tube 301 to be secured without causing compression or fluid occlusion. Further, connection of the IV tube 301 to the tube window and the rib tube channel 444 causes the connected IV tube 301 to be placed in a horizontal orientation, which enables a roof of the door 304 to close over the top end 320 without scratching, pulling, or otherwise mechanically affecting the IV tube 301.

Figure 5:
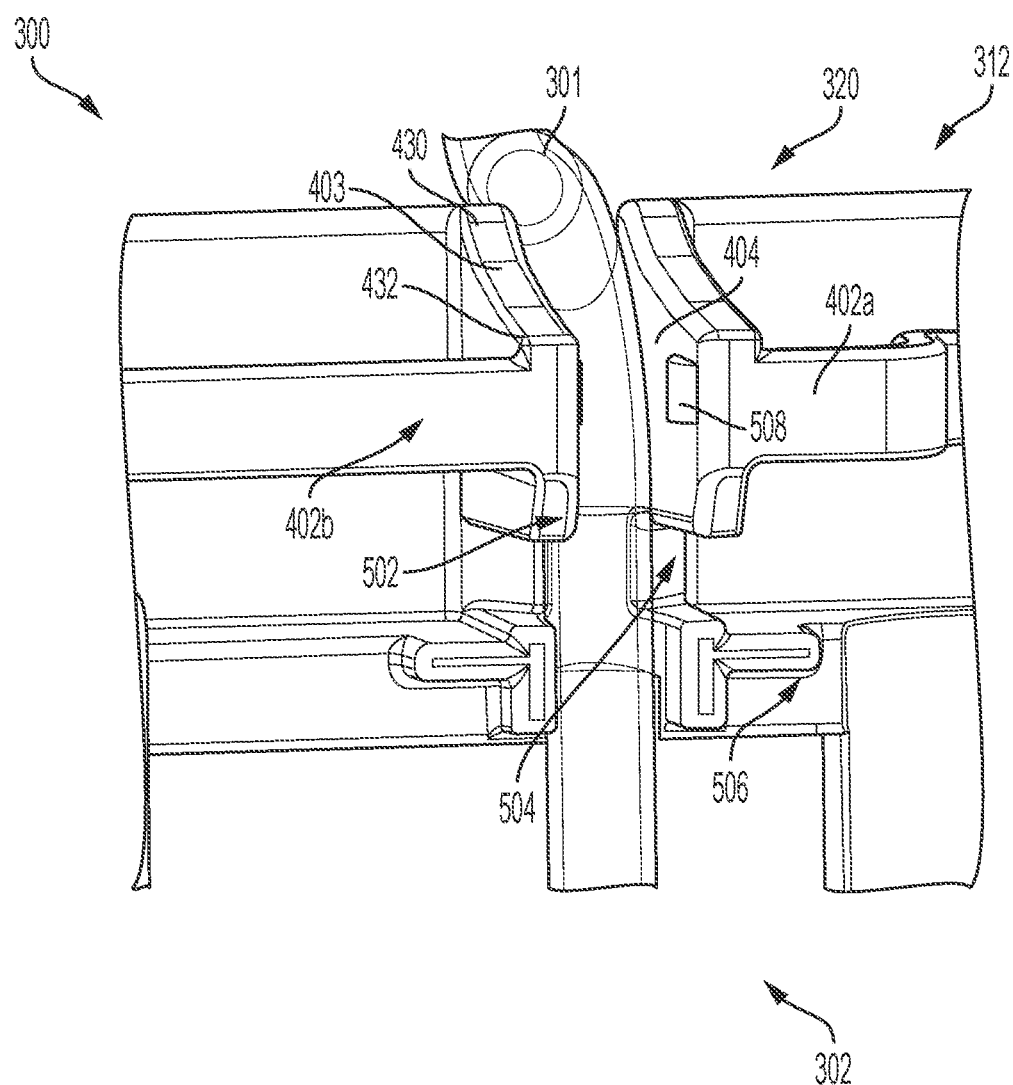

FIG. 5 is another diagram of the self-alignment features provided at the top end 320 of the actuation area 302 of the infusion pump 300, according to example embodiments of the present disclosure. In this diagram, the slope of the height of the hood rails 403 is more apparent from the first end 430 to the second end 432, which generally follows a bend in the IV tube 301. In the illustrated embodiment, the hoods 402 also include respective hood rails 502 that are configured to direct and retain the IV tube 301 within the tube channel 404. The example infusion pump 300 also includes a gap 504 separating the hood rails 502 from inner door guide ribs 506. The guide ribs 506 are configured to further secure and retain the IV tube 301 and prevent door closure if the IV tube 301 is misplaced.

Together, the hood rails 502, the gap 504, and the guide ribs 506 are configured to mate with corresponding self-alignment features on the door 304. For example, a v or u-shaped guide 706, shown in FIG. 7, is configured to fit within the gap 504 defined by the rails 502 and the ribs 506. The guide 706 on the door 304 may also be sized and/or shaped to mate or otherwise become flush with at least portions of the hood cavity 708 and/or pre-alignment guides 704 to retain the IV tube 301 and place and/or prevent the door 304 from closing if the IV tube 301 is at least slightly misaligned or outside of the tube channel 404.

The example infusion pump 300 also includes at least one retention knob 508 located on an inside wall of the hood rail 403. A retention knob 508 may be located on each hood rail 403. In some embodiments, the retention knob 508 may be integrally formed with the hood rail 403. In other embodiments, the retention knob 508 may be physically connected to the hood rail 403 via one or more chemical or mechanical fasteners.

Figure 6:
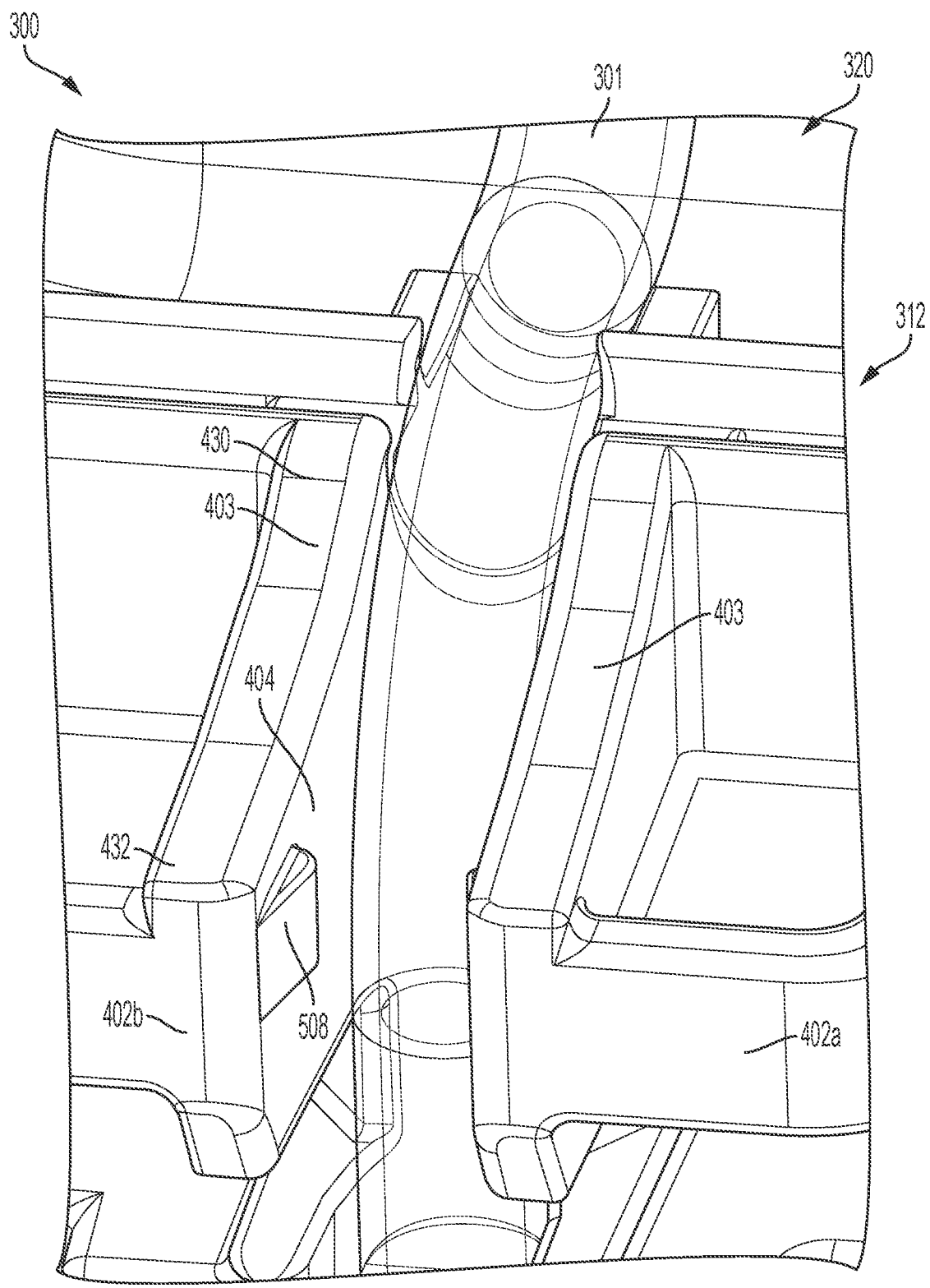

FIGS. 5 and 6 show diagrams of the retention knob 508, which includes a tab that extends outwardly from the hood rail 403 and into the tube channel 404. The retention knob 508 is positioned near an entrance of the tube channel 404 and configured to retain the IV tube 301 within the tube channel 404. The retention knob(s) 508 accordingly prevents the IV tube 301 from kinking when the door 304 is closed. The retention knob(s) 508 also help to retain the IV tube 301 when the tube is loaded into the tube channel 404.

FIG. 7 is a diagram of self-alignment features provided in the door 304 of the infusion pump 300, according to an example embodiment of the present disclosure. In the illustrated example, the door 304 includes a roof 702 that is configured to contact and cover the top end 320 of the actuation area 302 of the infusion pump 300, including the seal section 440. The roof 702 includes a roof tube channel 703 that is configured to align with and operate with the tube channel of the seal section 440 to enclose or otherwise contact the IV tube 301, thereby preventing containments from entering the actuation area 302.

The example roof 702 includes self-alignment features including lower pre-alignment guides 704, a v-guide 706, a door hood cavity 708, upper pre-alignment guides 710, and a pusher 712. A curved lip 701 is also configured to assist with pre-alignment of the IV tube 301. At least a portion of a top side of the example lower pre-alignment guide 704 is configured to contact (or at least be positioned adjacent to) an underside of the hoods 402 and/or an underside of the hood rails 403 when the door 304 is in the closed position. In addition, at least a portion of a bottom side of the lower pre-alignment guide 704 is configured to contact (or at least be positioned adjacent to) a top side of the inner door guide ribs 506 when the door 304 is in the closed position. Moreover, when the door is in the closed position, the under-hood rails 502 are configured to engage or slide within cutouts 720 in the lower pre-alignment guide 704 that are adjacent to the v-guide 706.

The example v-shaped guide 706 (e.g., a guide section) is configured to at least partially enclose the IV tube 301 between the locations of the rails 502 and the ribs 506 (i.e., the vertical portion of the ribs 506). Accordingly, the guide 706 additionally retains the IV tube 301 while preventing kinking or bending. Further, the interlocking or overlap between the rails 502, ribs 506, v-guide 706, and guide 704 makes it virtually impossible for the door 304 to be closed if the IV tube 301 is at least slightly misaligned. While the example embodiment shows a v-shaped guide 706, it should be appreciated that in other embodiments the guide 706 may have a U-shape, a triangular shape, etc. to at least partially encircle or enclose the IV tube 301.

In some embodiments, the example roof 702 of FIG. 7 may include the door hood cavity 708. The example door hood cavity 708 is configured to accommodate the respective hoods 402 and/or the hood rails 403. The cavity 708 may have dimensions that align or confirm to dimensions of the hoods 402 and/or the hood rails 403 to enable the hoods 402 and/or the hood rails 403 to fit within the cavity 708. The door hood cavity 708 combined with the hoods 402 and/or the hood rails 403 create an interlocked or overlapping structure when the door 304 is moved to a closed position. Any IV tube misalignment causes the IV tube to be positioned on one of the hoods 402 and prevents the hoods 402 from being able to be pushed into the respective cavities 708. The positioning accordingly prevents the door 304 from closing.

The example roof 702 of FIG. 7 may also include the upper pre-alignment guide 710 in some embodiments. A bottom face of the upper pre-alignment guide 710 is configured to cover and/or come in contact with a top face of the hoods 402 and/or hood rails 403 when the door 304 is moved to the closed position. The upper pre-alignment guide 710 may include channels 730 configured to engage with and/or accommodate the hood rails 403. The upper pre-alignment guide 710 provides further interlocking or overlap ribbed features that prevent the door 304 from closing if at least a portion of the IV tube 301 is misaligned or otherwise outside of the tube channel.

The example pusher 712 of FIG. 7 includes a channel that is adjacent to, connected to, and/or integrally formed with the roof tube channel 703. The channel has dimensions and a surface curvature sized and/or shaped to accept or otherwise enclose at least a top side of the IV tube 301. The pusher 712 has a radial curvature configured to accommodate or cause the bending of the IV tube 301 at the hood rails 403 within tube channel 404. In some embodiments, the pusher 712 is configured to operate in connection with the hood rails 402 to enclose and retain the IV tube within the tube channel 404 when the door 304 is moved to a closed position. The example pusher 712 is configured to prevent the IV tube 301 from extending upwards where it is bent between horizontal and vertical orientations. In some embodiments, the pusher 712 may apply force to the IV tube 301 causing it to be retained in the tube channel 404 when the door 304 is moved to the closed position.

Self-Alignment Embodiments

Figure 8:
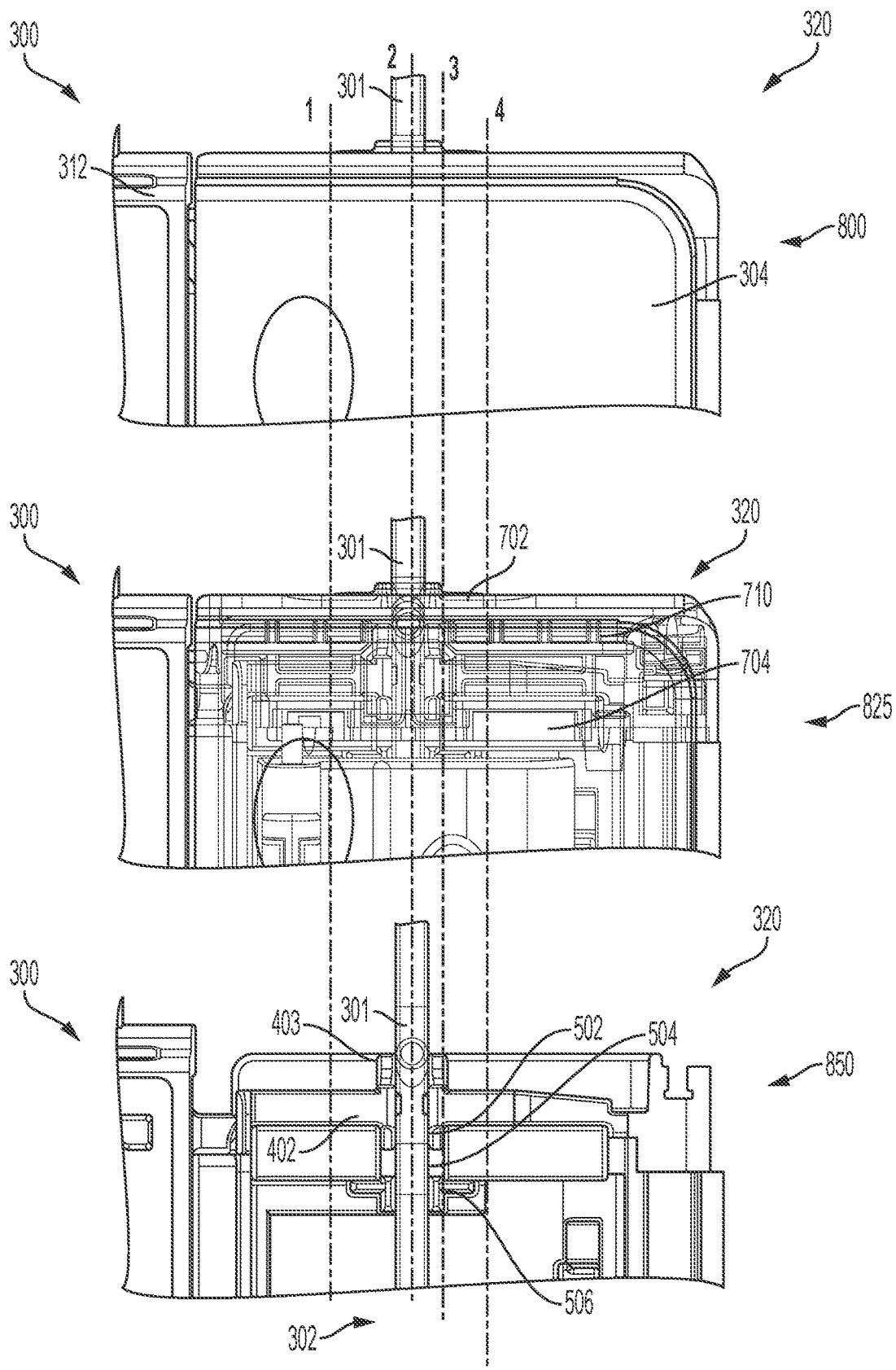
FIGS. 8 to 12 are cross-sectional diagrams of at least some of the self-alignment features described in connection with FIGS. 4 to 7, according to example embodiments of the present disclosure.

FIGS. 8 to 12 are cross-sectional diagrams of at least some of the self-alignment features described in connection with FIGS. 4 to 7 along longitudinal cut-lines (1), (2), (3), and (4), according to example embodiments of the present disclosure. FIG. 8 shows a diagram of a top end 320 of the infusion pump 300 with the door 304 in the closed position. A top diagram 800 shows the infusion pump 300 in solid, while a middle diagram 825 shows the infusion pump 300 with an outer cover of the door 304 made partially transparent. In addition, diagram 850 shows the infusion pump with a cover of the door 304 removed to expose the self-adjusting features including the hood 402, hood rails 403, rail 502, rib 506, gap 504, and pre-alignment guides 704 and 710.

Figure 9:
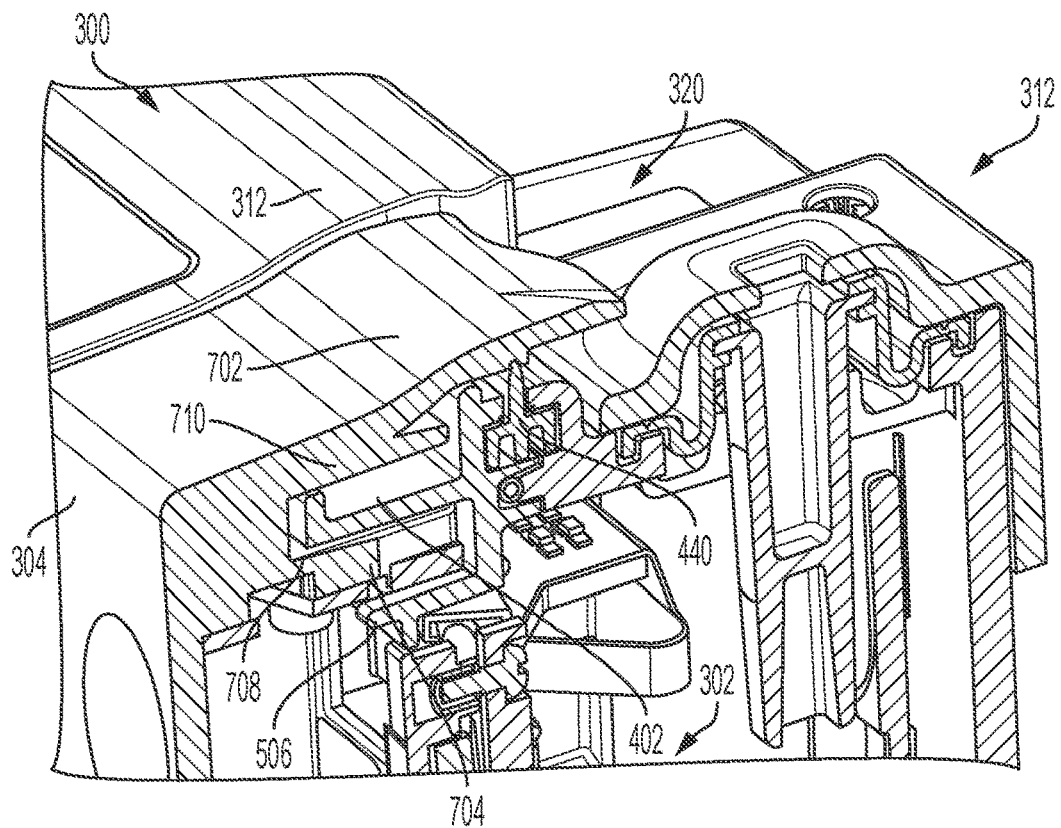
Figure 10:
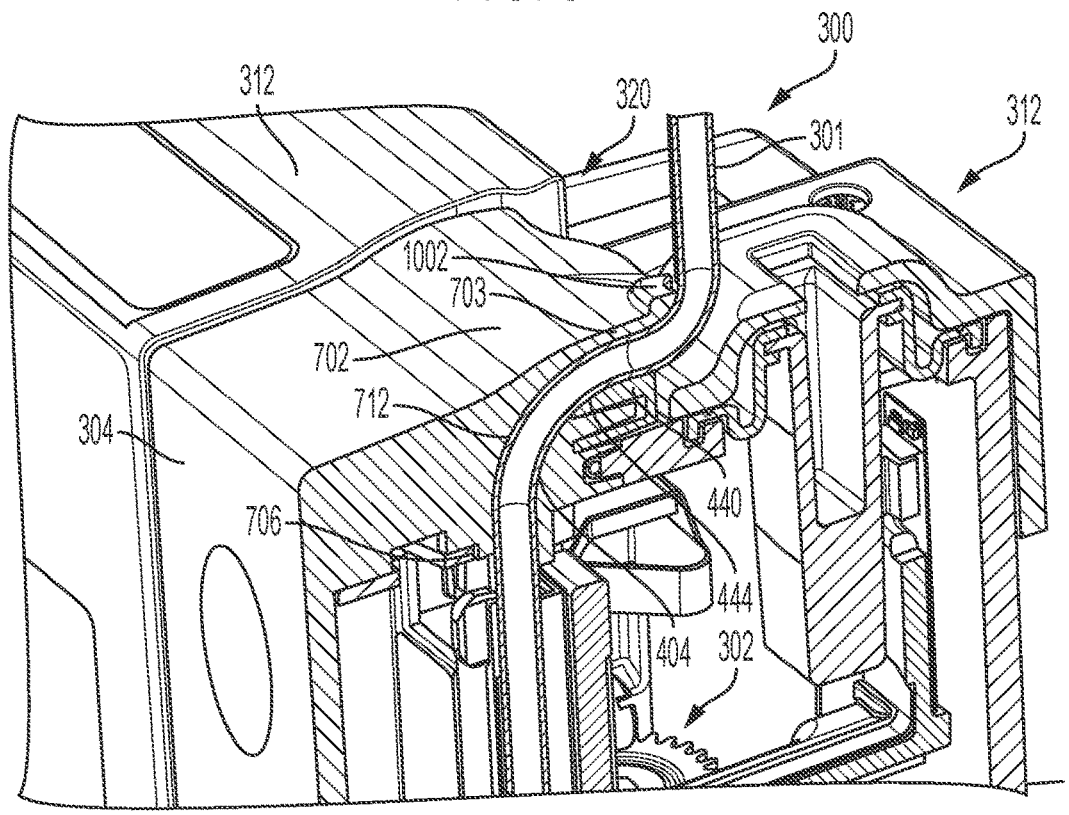
Figure 11:
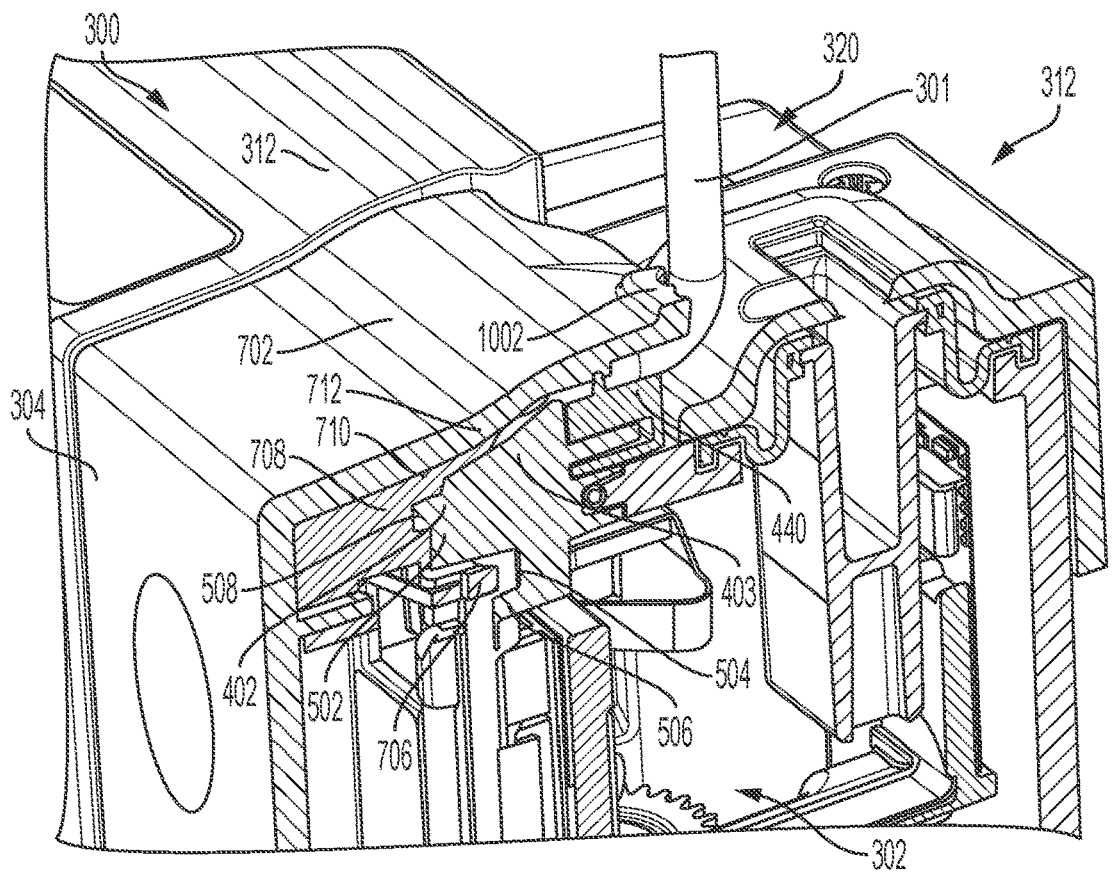
Figure 12:
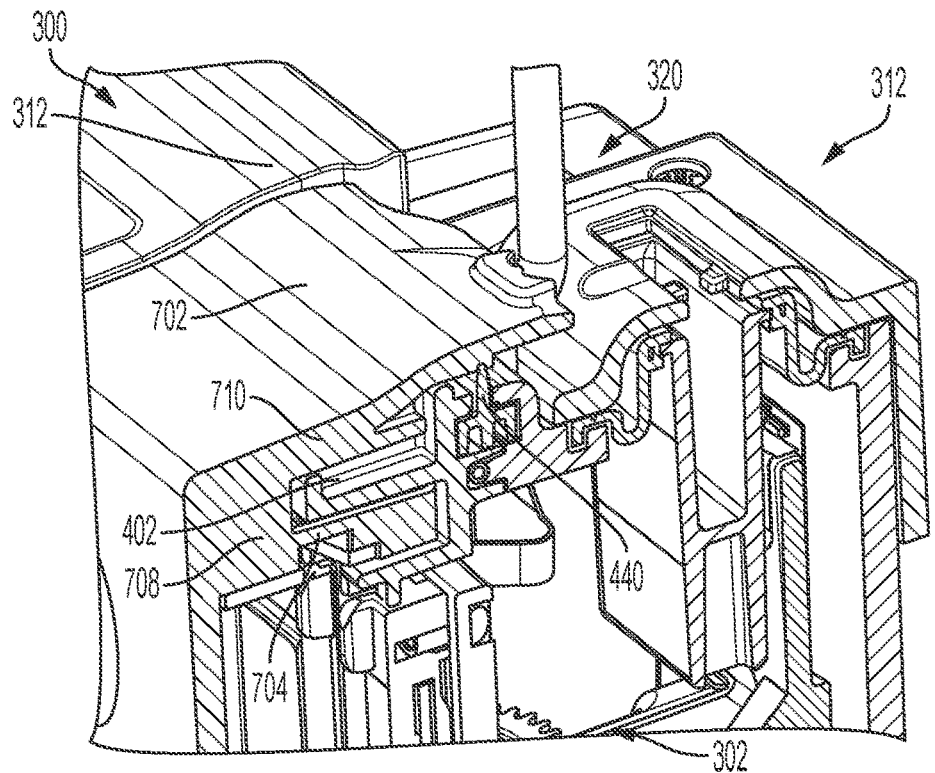

In the illustrated embodiment, cut line (1) corresponds to the cross-sectional perspective view shown in FIG. 9, cut line (2) corresponds to the cross-sectional perspective view shown in FIG. 10, cut line (3) corresponds to the cross-sectional perspective view shown in FIG. 11, and cut line (4) corresponds to the cross-sectional perspective view shown in FIG. 12.

FIG. 9 shows a cross-section of the infusion pump 300 along line (1) with the hood 402, gap 504, and ribs 506 being visible. The hood 402 is shown as being accommodated or placed within the cavity 708. The placement of the hood 402 in the cavity 708 causes the hood 402 to interlock or overlap with the upper pre-alignment guide 710 and the lower pre-alignment guide 704. The overlap between the hood 402 and guides 704 and 710 leave virtually no room for the IV tube 301. Thus, any misalignment of the IV tube 301 would prevent the door 304 from closing.

FIG. 9 also shows the roof 702 engaged with the seal section 440. The illustrated engagement prevents foreign containments from entering the actuation area 302. In addition, the engagement prevents the IV tube 301 from being misaligned at a top end 320 of the infusion pump 300.

FIG. 10 show a cross-section of the infusion pump 300 along line (2) at the IV tube 301. In the illustrated example, the seal section 440 includes a rib tube channel 444 that is configured to cradle at least a bottom side of the IV tube 301. The seal section 440 operates with the pusher 712 to enclose the IV tube 301 and cause at least a portion of the tube 301 to bend from a horizontal orientation (just under the roof 702) to a vertical orientation in the actuation area 302. The example pusher 712 also operates in connection with the tube channel 404 to further enclose the IV tube 301 at the bend. The pusher 712 and the v-guide 706 help retain the IV tube 301 in place. A roof lip 1002 in conjunction with the roof channel 703 causes at least a portion of the IV tube 301 to bend from a vertical or angled orientation just before entering the roof 702 to the horizontal orientation (just under the roof 702).

FIG. 11 shows a cross-section of the infusion pump 300 along cut line (3), which is provided along the hood rail 403. In the illustrated example, a cross-section of the hood rail 403 is visible in addition to the hood 402, the under-hood rail 502, the gap 504, the inner door guide ribs 506, the upper pre-alignment guide 710, the door hood cavity 708, and the v-guide 706. The self-alignment features shown in FIG. 11 create an overlapping or interlocked structure that leaves minimal or no gaps when the door 304 is moved to a closed position. Accordingly, the illustrated self-alignment features prevent the door 304 from closing if at least a portion of the IV tube 301 is misaligned.

FIG. 12 shows a cross-section of the infusion pump 300 along cut line (4), which is similar to cut line (1) but on an opposite side of the IV tube 301. In the illustrated example, the hood 402, the cavity 708, the upper pre-alignment guide 710, and the lower pre-alignment guide 704 are illustrated as being overlapping for interlocking. The overlap between the hood 402 and guides 704 and 710 leave virtually no room for the IV tube 301. Accordingly, any misalignment of the IV tube 301 prevents the door 304 from closing.

Figure 13:
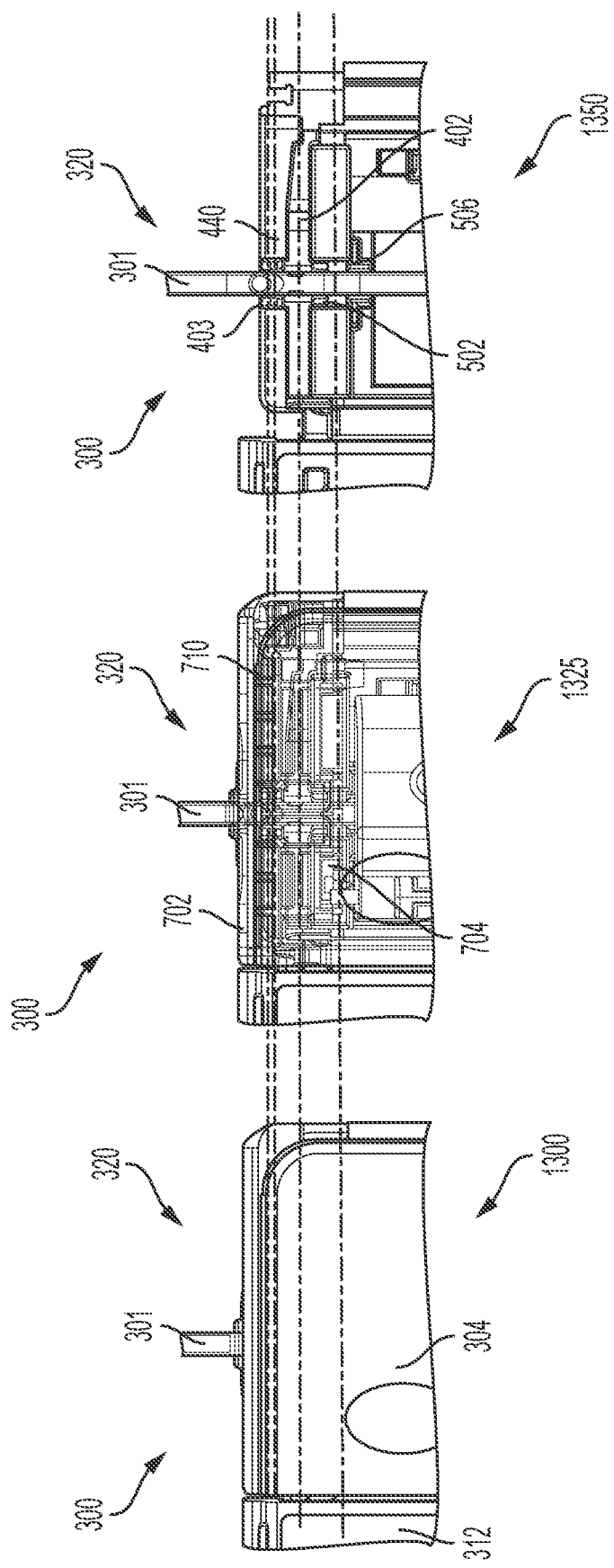
FIGS. 13 to 17 are cross-sectional diagrams of at least some of the self-alignment features described in connection with FIGS. 4 to 7, according to example embodiments of the present disclosure.

FIGS. 13 to 17 show different embodiments of at least some of the self-alignment features described above for lateral cut-lines (1), (2), (3), and (4). FIG. 13 is a diagram of a top end 320 of the infusion pump 300 with the door 304 in the closed position. A left diagram 1300 shows the infusion pump 300 in solid, while a middle diagram 1325 shows the infusion pump 300 with an outer cover of the door 304 made partially transparent. In addition, diagram 1350 shows the infusion pump with a cover of the door 304 removed to expose the self-adjusting features including the hood 402, the hood rails 403, the rail 502, the guide rib 506, the gap 504, and the pre-alignment guides 704 and 710.

Figure 14:
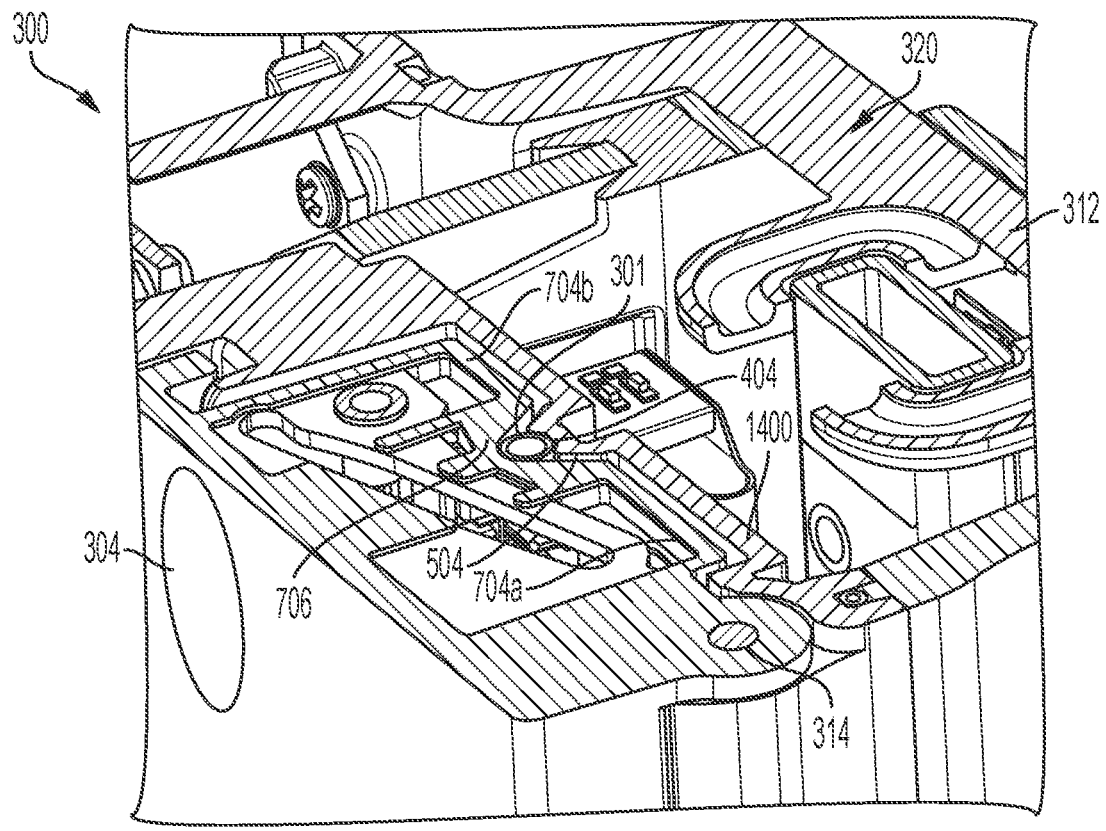

FIG. 14 shows a cross-section of the infusion pump 300 along lateral cut line (1), which runs through the v-guide 706 and the lower pre-alignment guide 704. The illustrated example shows the v-shaped profile of the guide 706 connected to or integrally formed with the lower pre-alignment guides 704a and 704b. The illustrated example also shows the tube channel 404 providing support for a bottom side of the IV tube 301 at the gap 504. Together, the tube channel 404 and the v-guide 706 retain the IV tube 301 in place. The v-shape of the guide 706 provides guidance or alignment such that the IV tube 301 is directed to a center of the v-shape when the door 304 is moved to a closed position, thereby ensuring the IV tube 301 is aligned and retained between the tube channel 404 and the guide 706.

As illustrated, there is minimal space between the guides 704 and 706 and a wall 1400 of the infusion pump 300 housing 312 as a result of the overlapping or interlocking configuration of the guides 704 and 706 and the wall 1400 at the gap 504. This interlocking configuration prevents the door 304 from closing if at least a portion of the IV tube 301 is misaligned.

Figure 15:
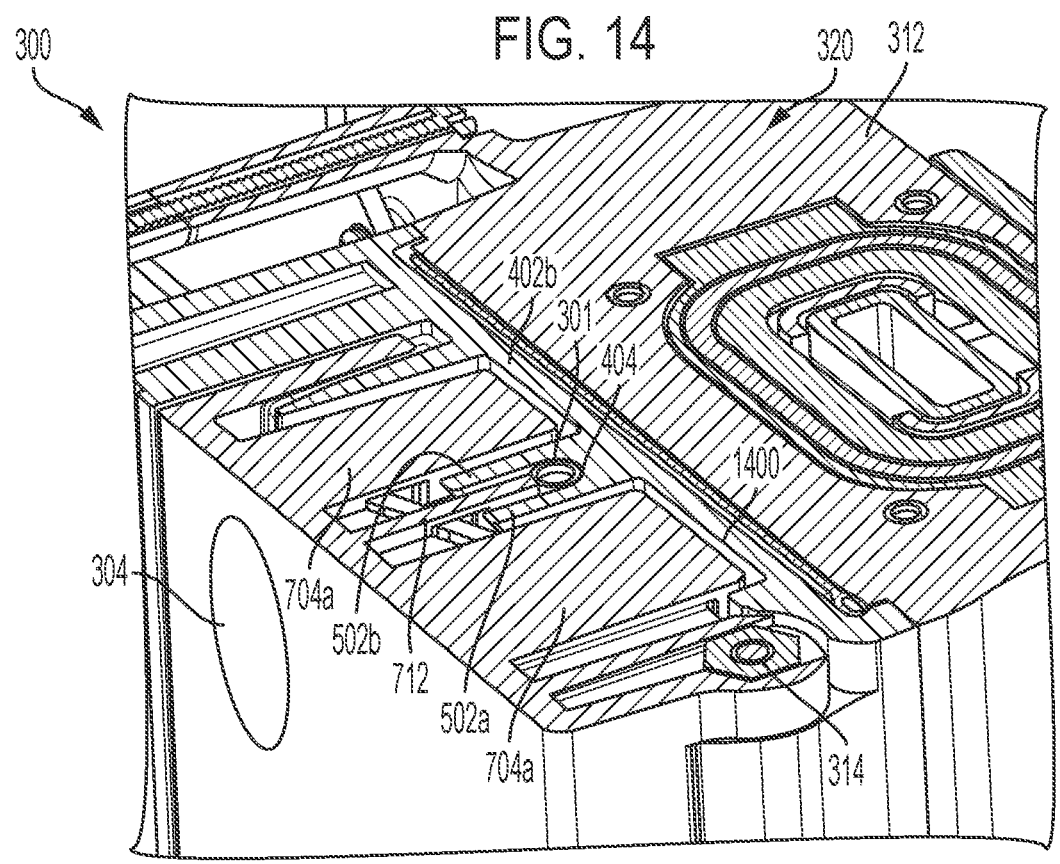

FIG. 15 is a diagram of a cross-section of the infusion pump 300 along lateral cut line (2), which runs through the under-hood rail 502 and the lower pre-alignment guide 704. The illustrated example shows the overlapping or interlocking between the lower pre-alignment guide 704, the under hood rail 502, and the wall 1400 of the infusion pump 300. The minimal spacing (if any) between the lower pre-alignment guide 704, the under hood rail 502, and the wall 1400 prevents the door 304 from closing if the IV tube 301 is misaligned.

The illustrated example also shows the pusher 712 retaining the IV tube 301 in place within the tube channel 404. The u-shaped profile of the under-hood rail 502 in conjunction with the protrusion of the pusher 712 causes the IV tube 301 to be pushed against and retained within the tube channel 404 when the door 304 is moved to a closed position. After the door 304 is closed, the pusher 712 prevents the IV tube 301 from becoming displaced.

Figure 16:
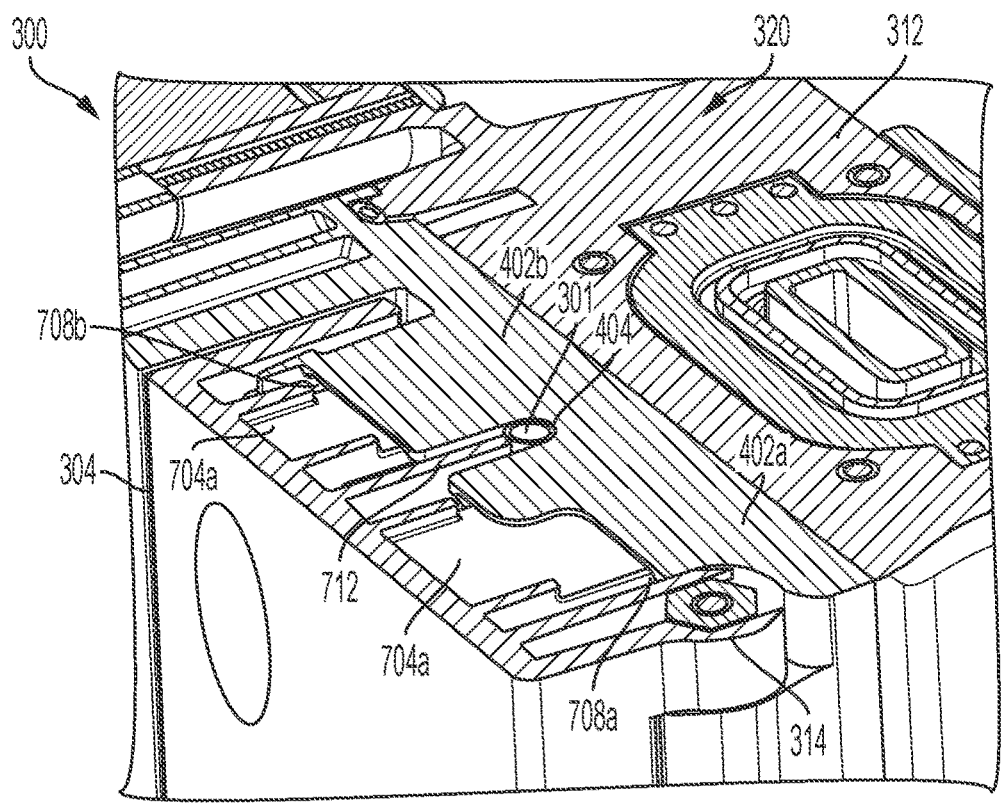

FIG. 16 shows a cross-section of the infusion pump 300 along lateral cut line (3), which runs through the hood 402, the tube channel 404, and the door hood cavity 708. The illustrated example shows a guiding wave profile of the hood 402, which is configured to assist the v-guide 706 for capturing the IV tube 301 in relation to the pusher 712. The opening provided by the hood 402 (between the sides 402 and 402b) is configured to direct the IV tube 301 to the tube channel 404. When the door 304 is closed, the pusher 712 contacts the other side of the IV tube 301, thereby retaining the tube against the tube channel 404.

The illustrated embodiment also shows the hood 402 contacting the cavity 708. As shown in FIG. 16, there is minimal or no space between the hood 402 and the cavity 708, which is defined in part by the lower pre-alignment guide 704. The overlap or interlocking between the hood 402 and the cavity 708/lower pre-alignment guide 704 prevents the door 304 from closing when the IV tube 301 is misaligned.

Figure 17:
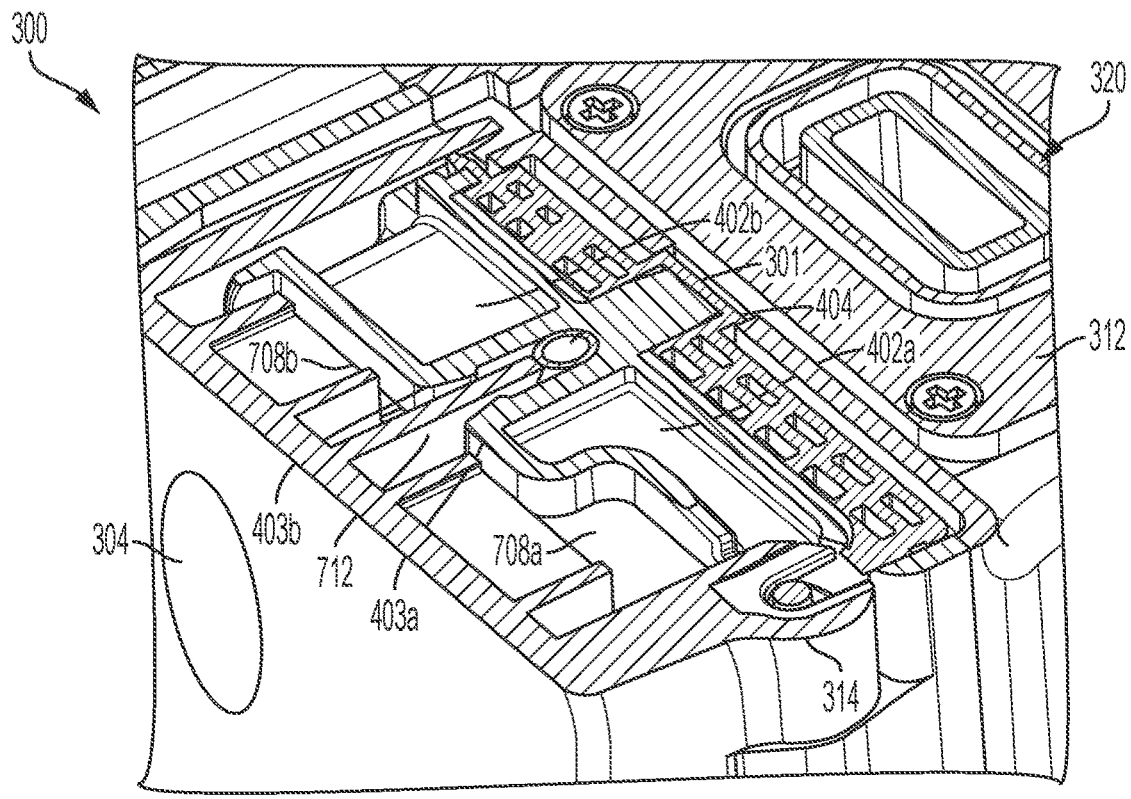

FIG. 17 shows a cross-section of the infusion pump 300 along lateral cut line (4), which runs through the hood 402 and the hood rail 403. The illustrated example shows again the guiding wave profile of the hood 402 in addition to the profile of the hood rails 403. As discussed above, the opening provided by the hood 402 and defined by the hood rails 403 is configured to direct the IV tube 301 to the tube channel 404 so that when the door 304 is closed, the pusher 712 contacts the other side of the IV tube 301, thereby retaining the tube against the tube channel 404.

The illustrated embodiment also shows the hood 402 contacting the cavity 708. As shown in FIG. 16, there is minimal or no space between the hood 402, and the cavity 708. The overlap or interlocking between the hood 402 and the cavity 708 prevents the door 304 from closing if the IV tube 301 is misaligned. Also, the retention knobs 508 are shown in FIG. 17, which hold the IV tube 301 in its place upon insertion.

Figure 18:
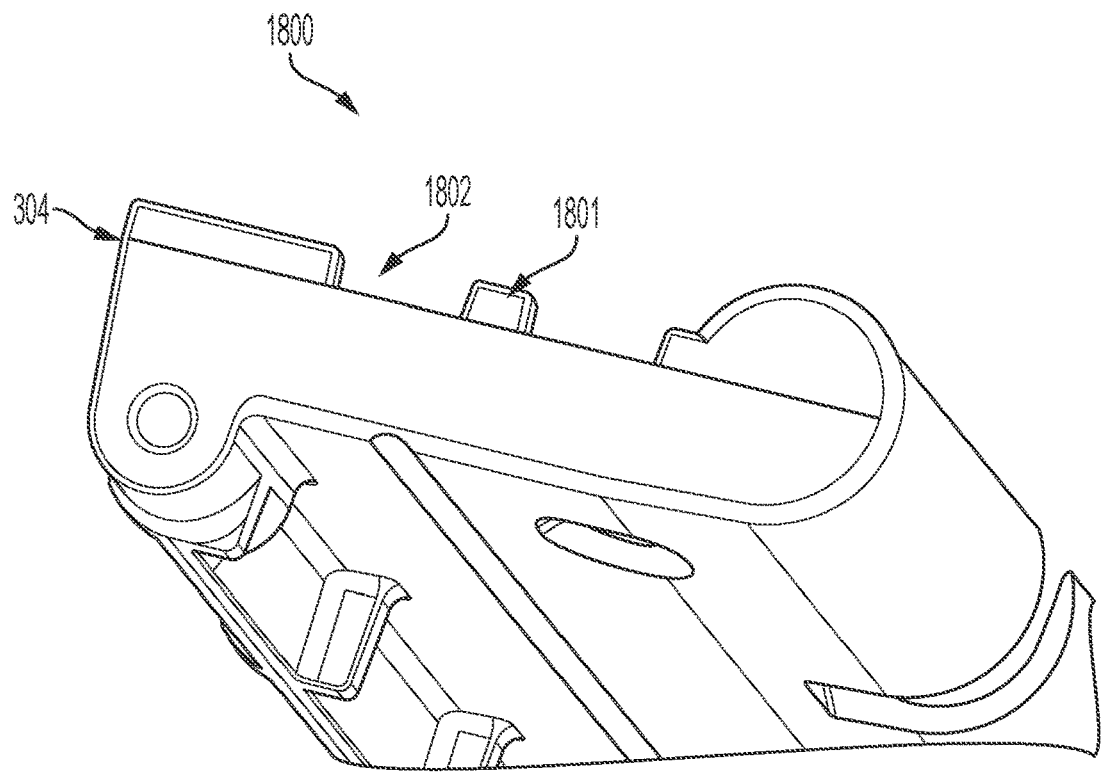
FIG. 18 is a diagram of self-alignment features of an interior portion of the door of the infusion pump of FIG. 3, according to an example embodiment of the present disclosure.

FIG. 18 shows a diagram of self-alignment features of an interior portion 1800 of the door 304, according to an example embodiment of the present disclosure. The features include a pusher 1801. The example pusher 1801 is configured to support the IV tube 301 in a bottom portion of the IV tube channel 404. The pusher 1801, in association with the vertical and horizontal portions of the guide ribs 506, prevent closure of the door 304 when the IV tube 301 is misaligned.

In addition, the features of FIG. 18 include reliefs 1802 configured to engage with front case rails 502 and/or the guide ribs 506. In some embodiments, the reliefs 1802 may engage the seal section 440. Together, the pusher 1801 and reliefs 1802 provide for IV tube alignment and retention.

Figure 19:
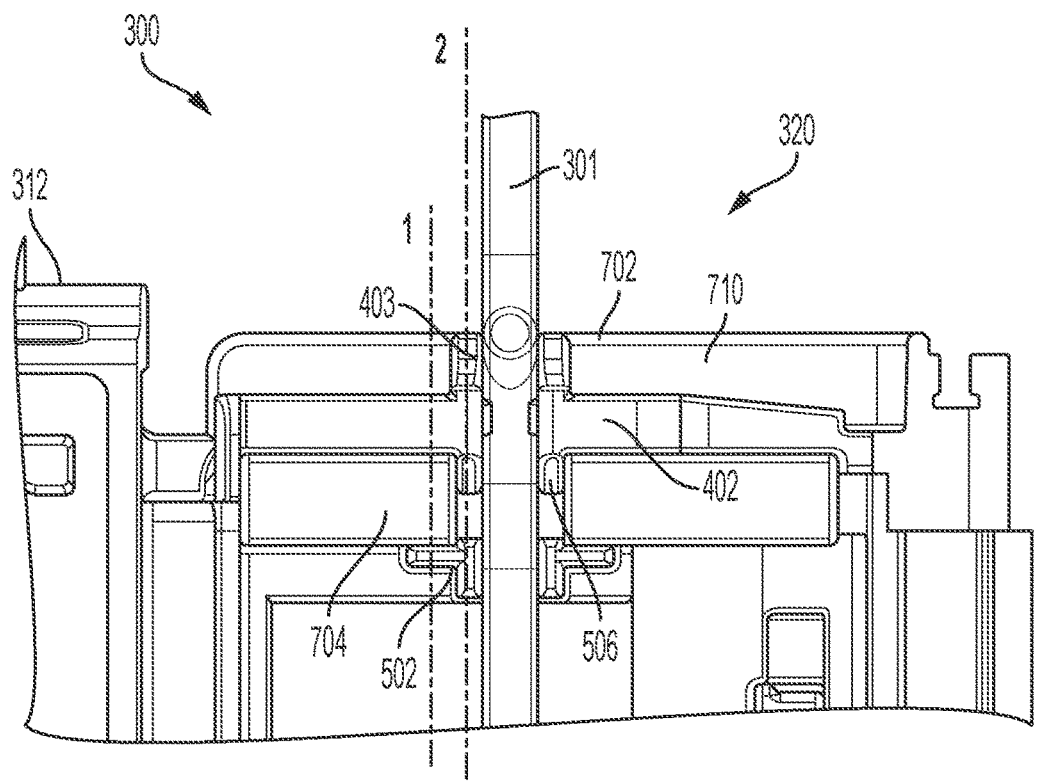
FIGS. 19 to 21 are diagrams of different embodiments of at least some of the self-alignment features described in connection with FIGS. 4 to 7, according to an example embodiment of the present disclosure.
Figure 20:
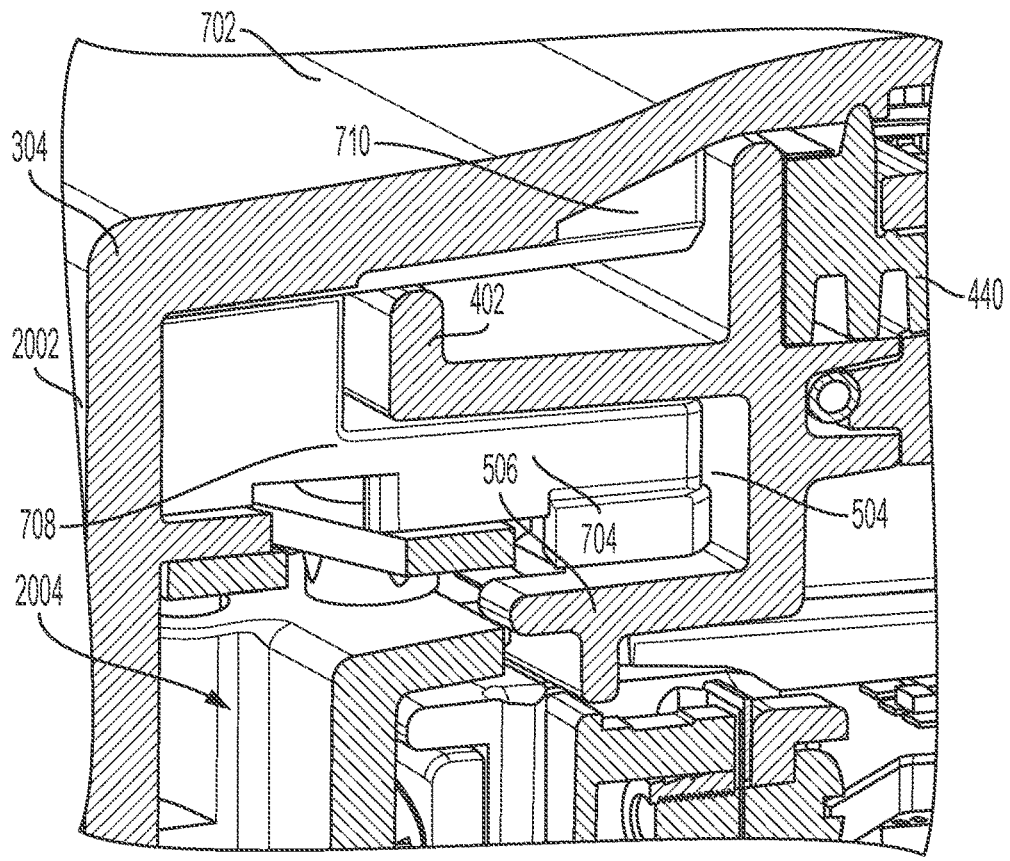
Figure 21:
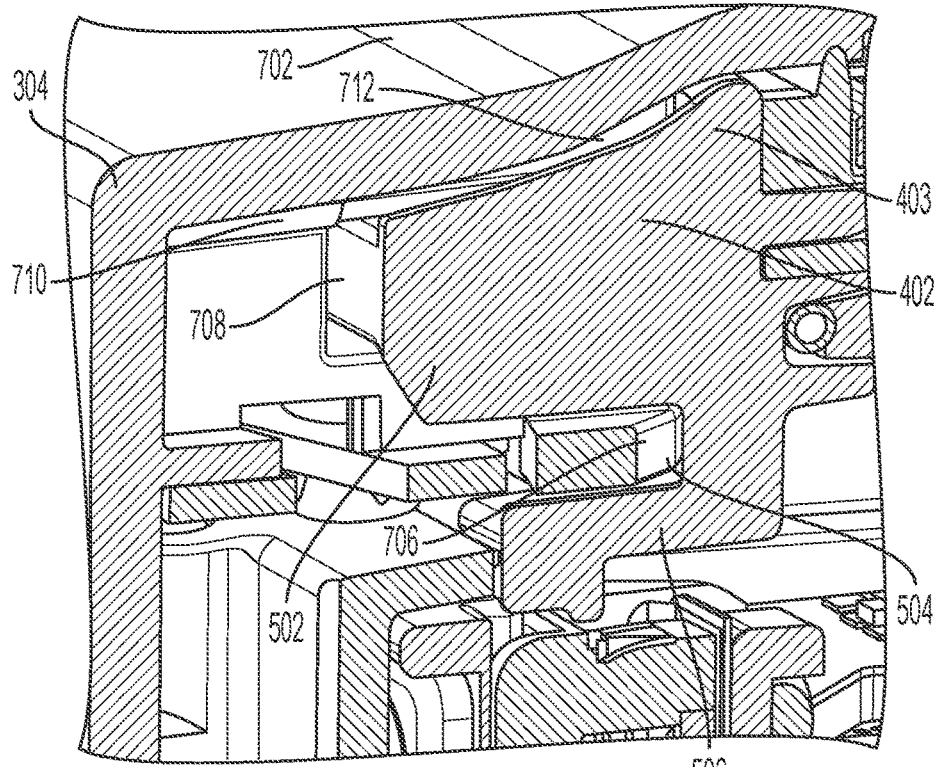

FIGS. 19 to 21 show different embodiments of at least some of the self-alignment features described in connection with FIGS. 4 to 7 above for longitudinal out-lines (1) and (2). FIG. 19 is a diagram of a top end 320 of the infusion pump 300 with the door 304 made transparent to expose the self-adjusting features including the hood 402, the hood rails 403, the rail 502, the guide rib 506, and the gap 504.

FIG. 20 shows a cross-section of the infusion pump 300 along line (1) with the hood 402, the gap 504, and the guide ribs 506 being visible. Similar to FIG. 9, the hood 402 is located in the door hood cavity 708 and overlaps or is interlocked with the upper pre-alignment guide 710 and the lower pre-alignment guide 704. In addition, the ribs 506 are adjacent to, overlap or are interlocked with, or otherwise contact the lower pre-alignment guide 704. The overlap between the hood 402, the ribs 506, and the guides 704 and 710 leaves virtually no room for the IV tube 301. Thus, any misalignment of the IV tube 301 prevents the door 304 from closing.

FIG. 20 also shows that the door 304 includes two distinct parts, an outer door 2002 and an inner door 2004. The outer door 2002 includes a casing or housing configured to enclosure and/or provide support for the inner door 2004. The example inner door 2004 includes, for example, the door hood cavity 708, the upper pre-alignment guide 710, and the lower pre-alignment guide 704 that provide internal tube self-alignment features. In some examples, the outer door 2002 and inner door 2004 may be formed from the same material as a single piece. In other examples, the outer door 2002 and the inner door 2004 are formed separately and mechanically connected together.

FIG. 21 shows a cross-section of the infusion pump 300 along cut line (2) along the hood rail 403. In the illustrated example, a cross-section of the hood rail 403 is visible in addition to the hood 402, the under-hood rail 502, the gap 504, the inner door guide ribs 506, the upper pre-alignment guide 710, the door hood cavity 708, and the v-guide 706. The self-alignment features shown in FIG. 21 create an overlapping, interlocked, or meshed structure that leaves minimal or no gaps when the door 304 is moved to a closed position. Accordingly, the illustrated self-alignment features prevent the door 304 from closing if at least a portion of the IV tube 301 is misaligned.

Figure 22:
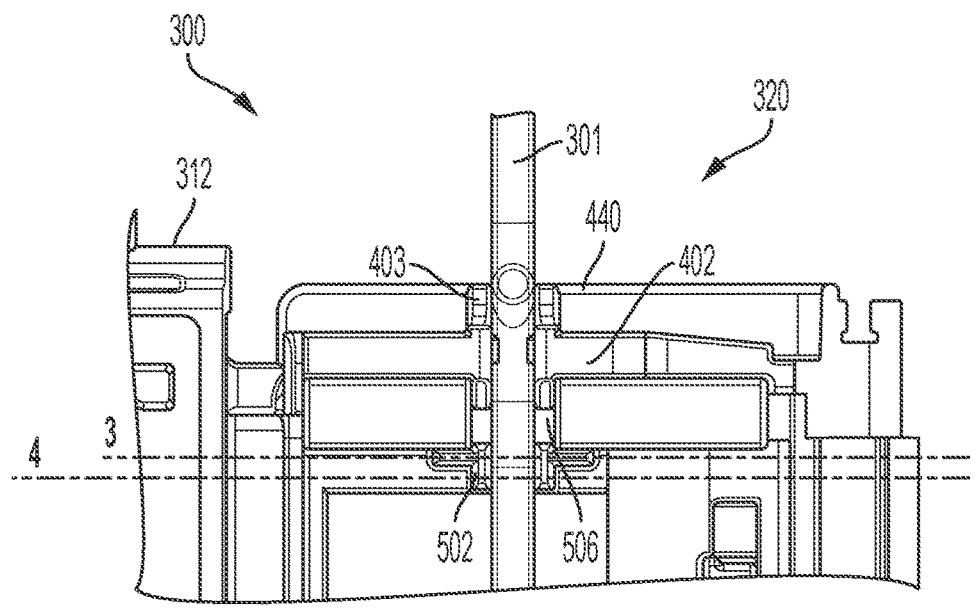
FIGS. 22 to 24 are diagrams of different embodiments of at least some of the self-alignment features described in connection with FIGS. 4 to 7, according to an example embodiment of the present disclosure.
Figure 23:
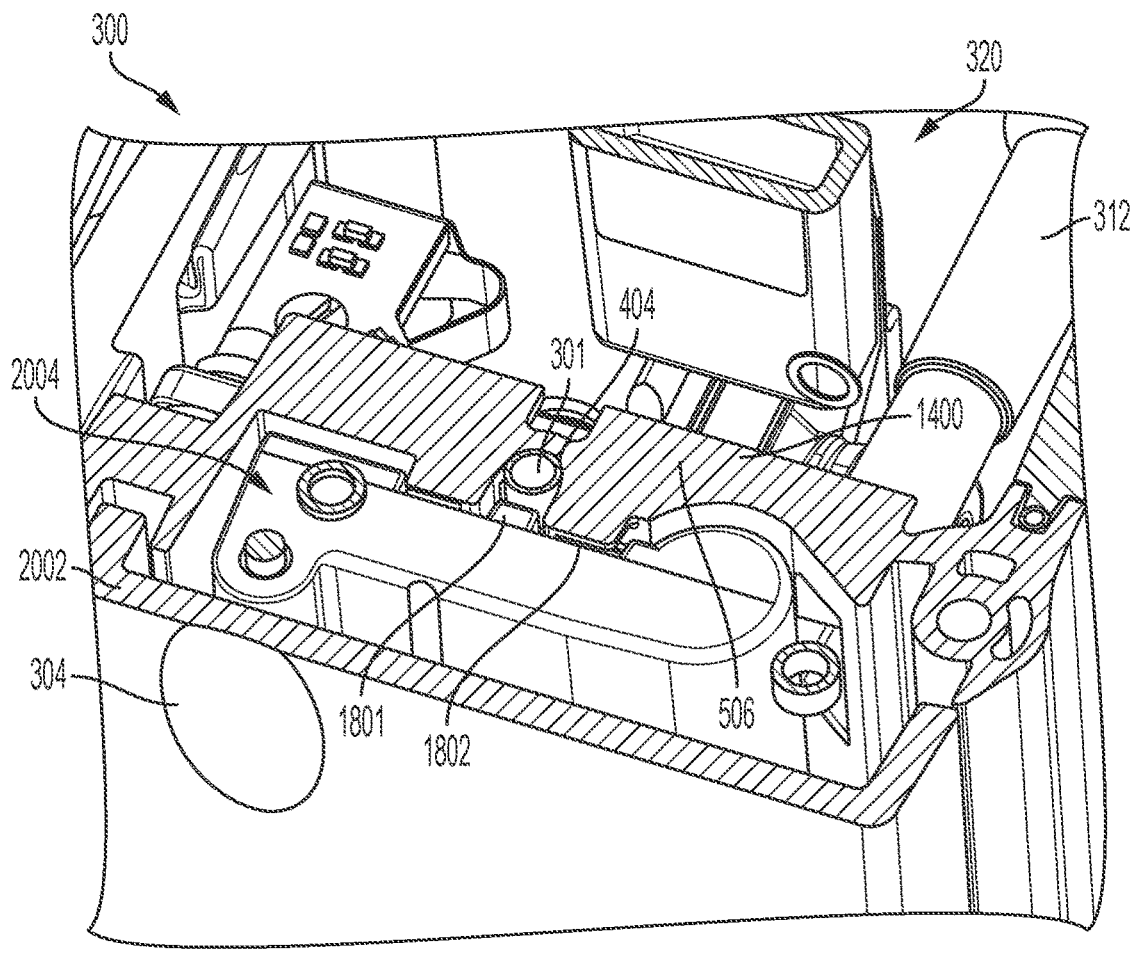
Figure 24:
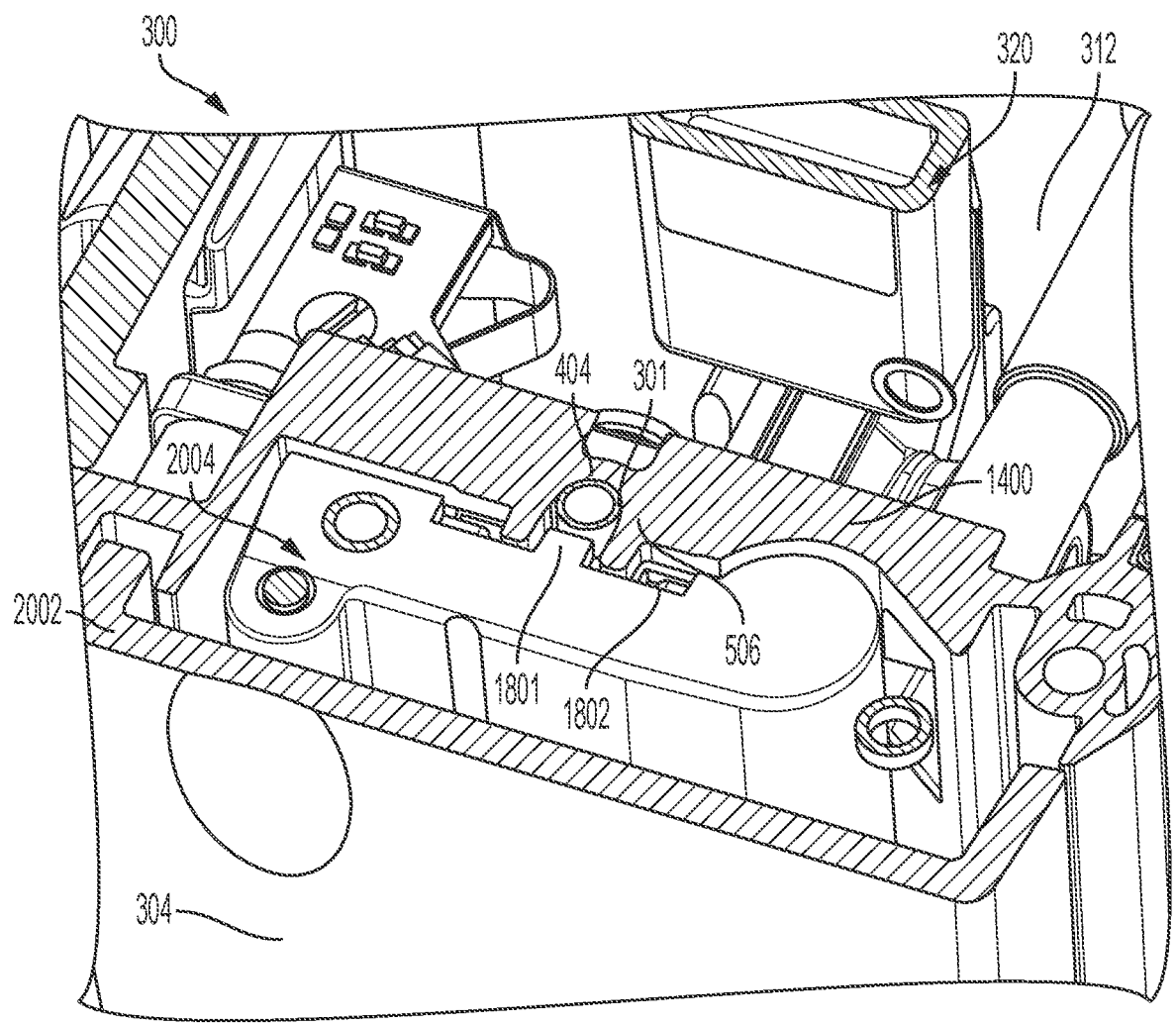

FIGS. 22 to 24 are diagrams of different embodiments of at least some of the self-alignment features described in connection with FIGS. 4 to 7 above for lateral cut-lines (3) and (4), according to an example embodiment of the present disclosure. FIG. 22 shows a diagram of a top end 320 of the infusion pump 300 with the door 304 made transparent to expose the self-adjusting features including the hood 402, hood rails 403, rail 502, rib 506, and gap 504.

FIG. 23 shows a cross-section of the infusion pump 300 along lateral cut line (3) of FIG. 22. The illustration includes a diagram of the inner door portion 1800 of the door 304 including the pusher 1801, as shown in FIG. 18. In this illustrated example, the inner door guide ribs 506 are configured to engage, interlock, contact, or otherwise mesh with reliefs 1802 of the inner portion 1801 of the door 304. The U-shaped cutout of the ribs 506 is configured to cause the IV tube 301 to self-align into the tube channel 404. When the door 304 is in the closed position, the pusher 1801 is configured to retain the IV tube 301 within the tube channel 404. The minimal spacing between the self-alignment features prevents the door 304 from closing if the IV tube 301 is misaligned. FIG. 23 also shows the outer door 2002 and the inner door 2004 sections.

FIG. 24 shows a cross-section of the infusion pump 300 along lateral cut line (4) of FIG. 22. In the illustrated example, the inner door guide ribs 506 are shown in proximity to the relief 1802 of the inner portion 1801 of the door 304. The figure shows the minimal spacing between the self-alignment features, which prevents the door 304 from closing if the IV tube 301 is misaligned. FIG. 24 further shows the outer door 2002 and the inner door 2004 sections.

Interlocking Ribs Embodiments

Figure 25:
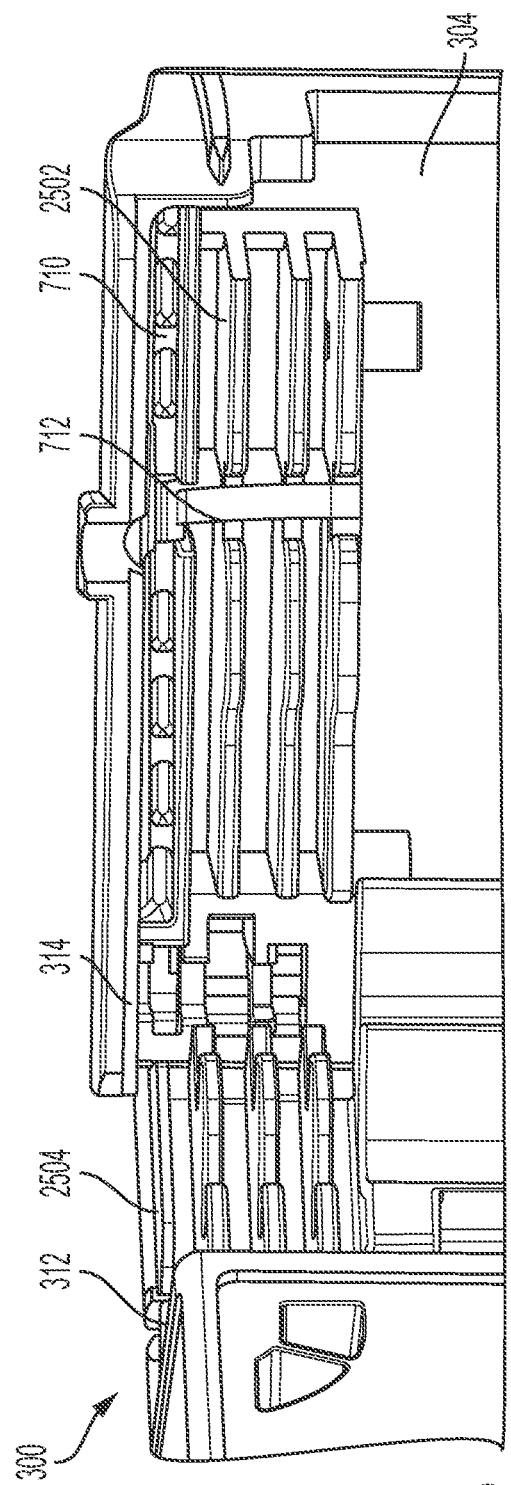
FIGS. 25 to 29 are diagrams of interlocking ribs self-alignment features of the infusion pump of FIG. 3, according to example embodiments of the present disclosure.
Figure 26:
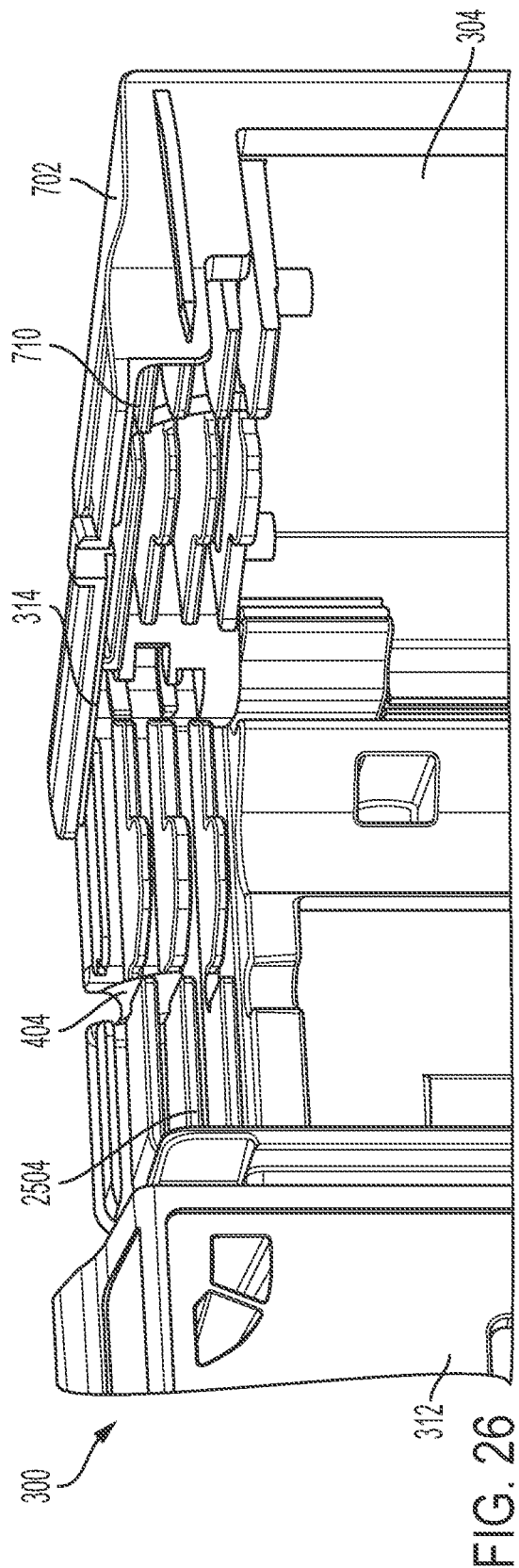

FIGS. 25 to 29 show diagrams of interlocking rib self-alignment features of the infusion pump 300 of FIG. 3, according to example embodiments of the present disclosure. FIGS. 25 and 26 are diagrams in which the door 304 is shown to include a set of interlocking ribs 2502 and the housing 312 of the infusion pump 300 includes interlocking ribs 2504. The door 304 also includes the pusher 712 and the upper pre-alignment guide 710.

The ribs 2502 of the door 304 may be similar to the guide 704 of FIG. 7, where the ribs 2502 are separated such that ribs 2502 on a first side are separated by the tube channel 404 from ribs on the other, second side. While the illustrated embodiment shows three ribs, it should be appreciated that other embodiments may include fewer or additional ribs. The thickness and shape of the ribs corresponds to spacing between the ribs 2504 such that the ribs 2504 are to fit within minimal gaps between the ribs 2502. In addition, spacing between the ribs 2504 is configured to accommodate the ribs 2502.

Figure 27:
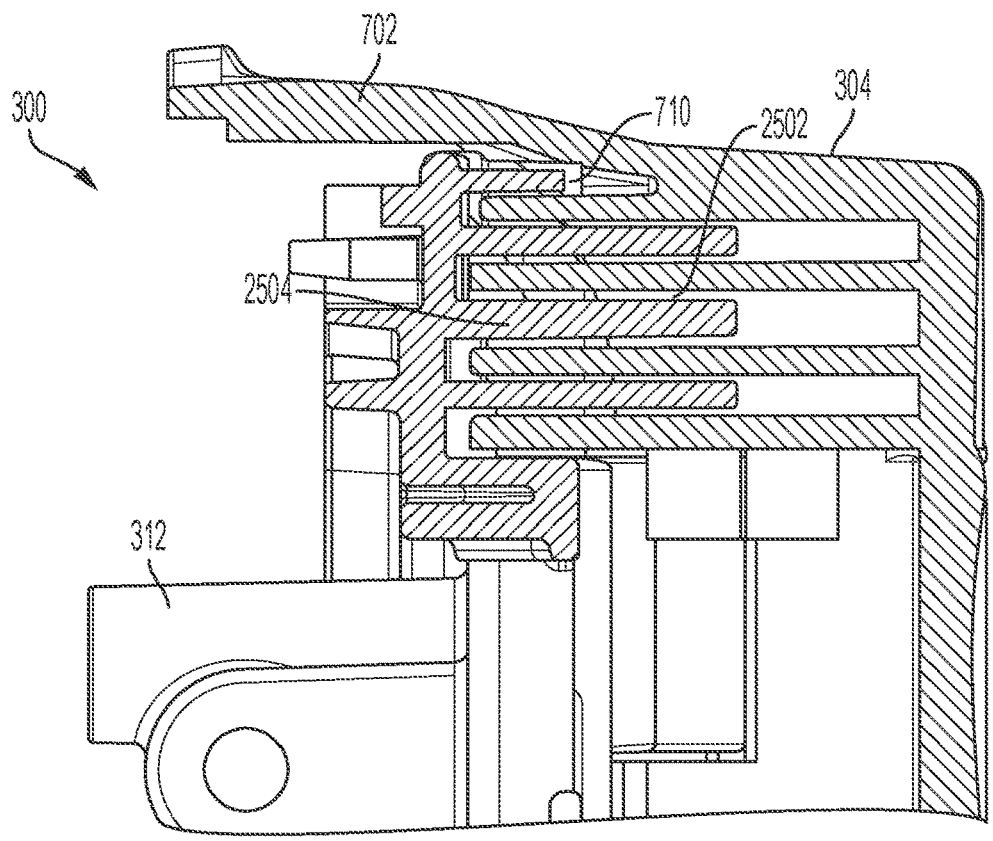
Figure 28:
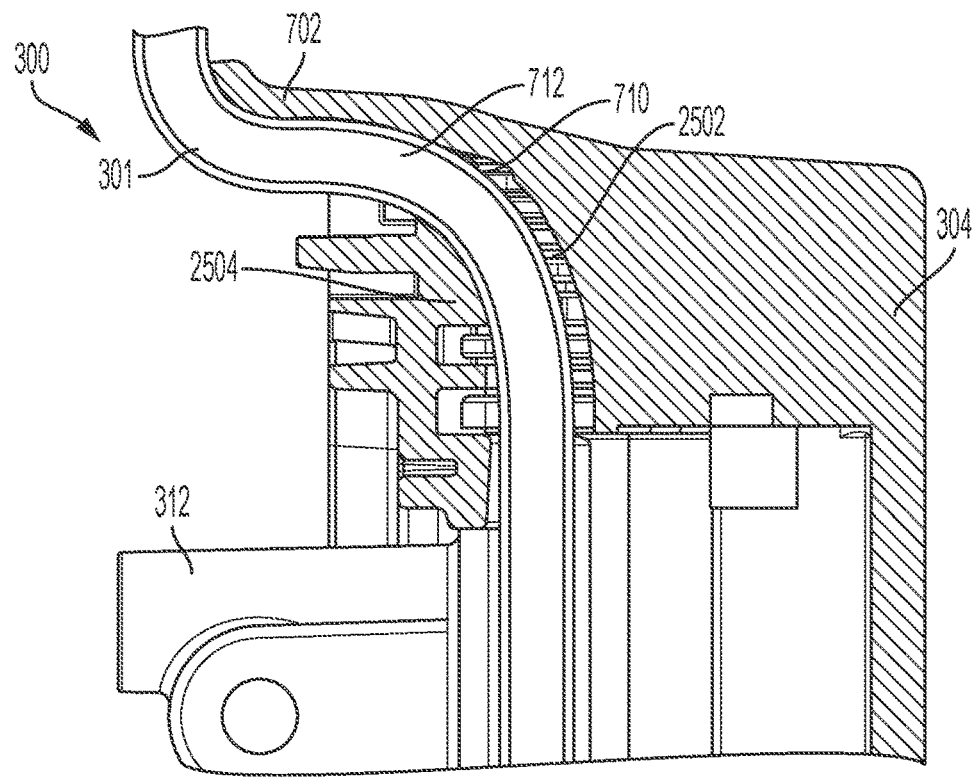
Figure 29:
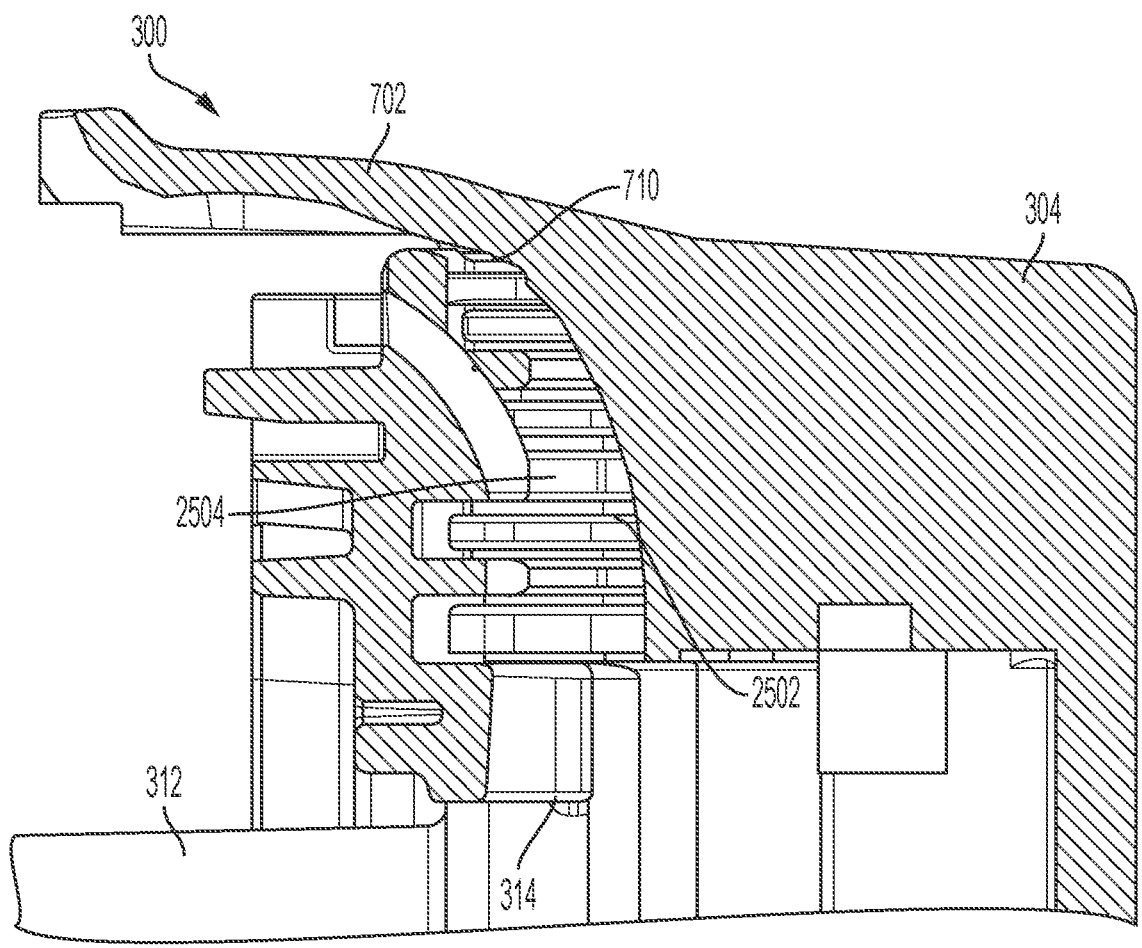

The example ribs 2502, 2504, and the guide 710 are configured to overlap or interlock when the door 304 is moved to a closed position. FIGS. 27 to 29 are diagrams of the door 304 in the closed position with the ribs 2502, 2504, and the guide 710 overlapping or being interlocked. As illustrated, there is minimal or no space for the IV tube 301 to kink or otherwise become misaligned. Any such misalignment of the IV tube 301 prevents the door ribs 2502, 2504, and the guide 710 from interlocking, and thus prevents the door 304 from closing. FIG. 29 additionally shows that the hinge 314 may include the ribs 2502 and 2504 to prevent the IV tube 301 from being crimped where the door 304 contacts the housing 312.

Alternative Self-Alignment Feature Embodiments

Figure 30:
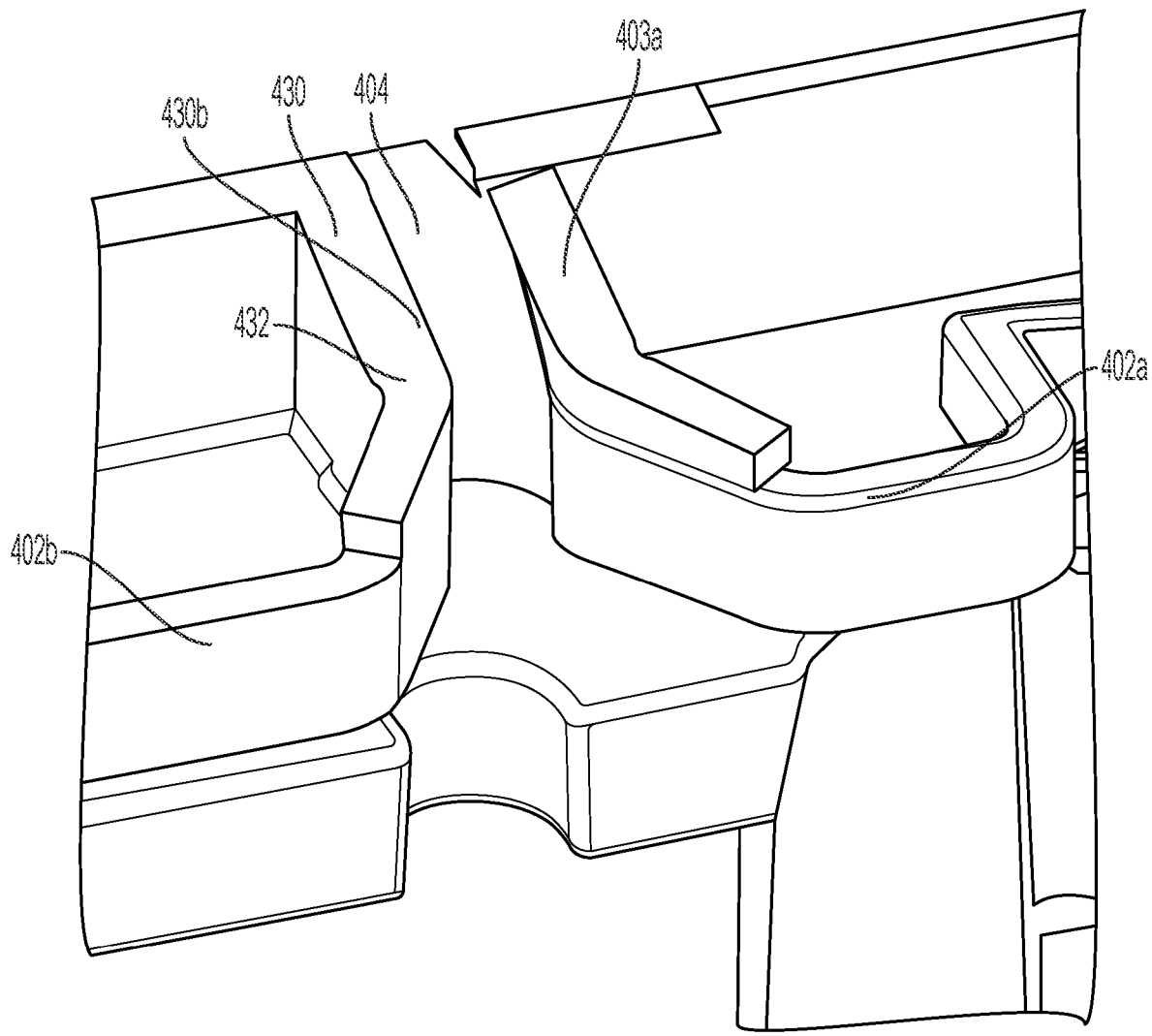
FIGS. 30 to 40 are diagrams that show alternative embodiments of at least some of the self-alignment features described in connection with FIGS. 4 to 7, according to example embodiments of the present disclosure.
Figure 31:
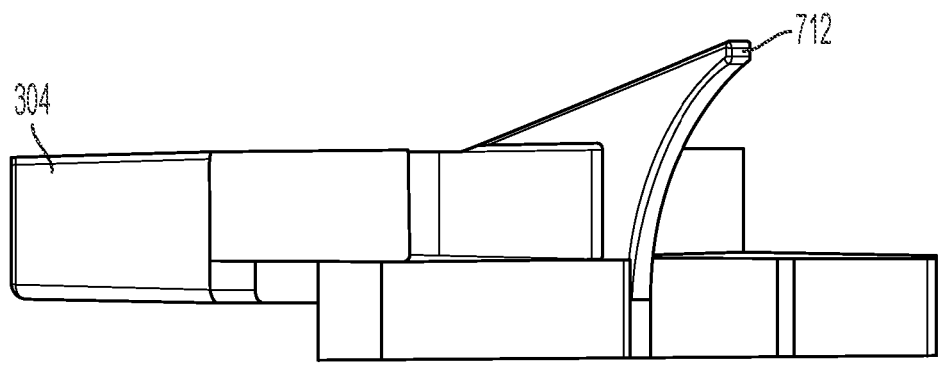

FIGS. 30 to 40 are diagrams that show alternative embodiments of the pusher 712, the tube channel 404, the hood 402, and the hood rails 403, according to example embodiments of the present disclosure. FIGS. 30 and 31 show diagrams of an embodiment where the pusher 712 is narrower and integrated into the door 304. In some embodiments, the components shown in FIG. 31 could be separate parts that are snapped/press fitted into the outer door cavity with a corresponding matching shape. In addition, the hood rails 403 are angled inward slightly toward the tube channel 404 to compensate for the reduced width of the pusher 712. The angling inward of the hood rails 403 helps retain the IV tube 301 in place. In addition, when the door 304 is closed, the pusher 712 is dimensioned to fit between the hood rails 403 and further retain the IV tube 304 in place.

Figure 32:
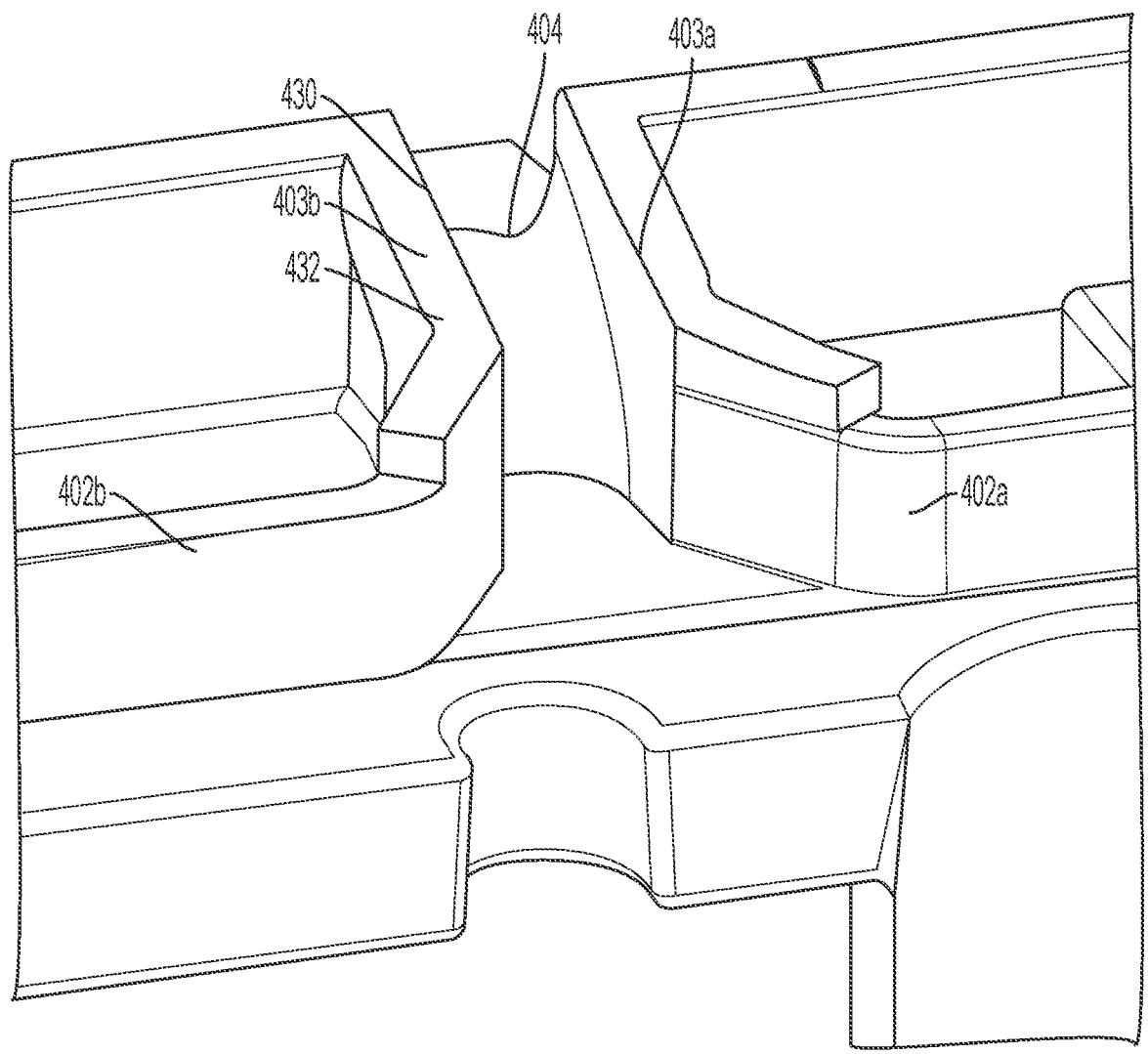
Figure 33:
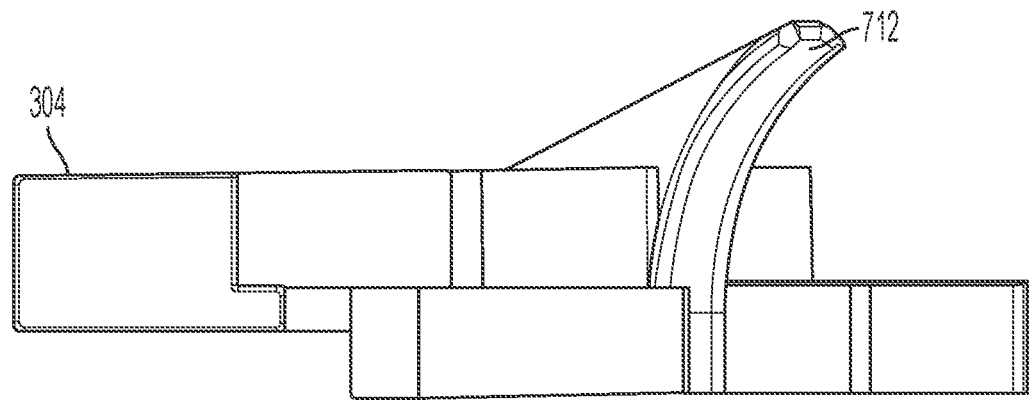

FIGS. 32 and 33 are diagrams of an embodiment where the pusher 712 is wider and integrated into the door 304. In addition, the hood rails 403 are angled outwardly slightly away the tube channel 404 to compensate for the increased width of the pusher 712. The angling outward of the hood rails 403 helps accommodate the wider pusher 712. When the door 304 is closed, the pusher 712 is dimensioned to fit between the hood rails 403 and retain the IV tube 304 in place.

Figure 34:
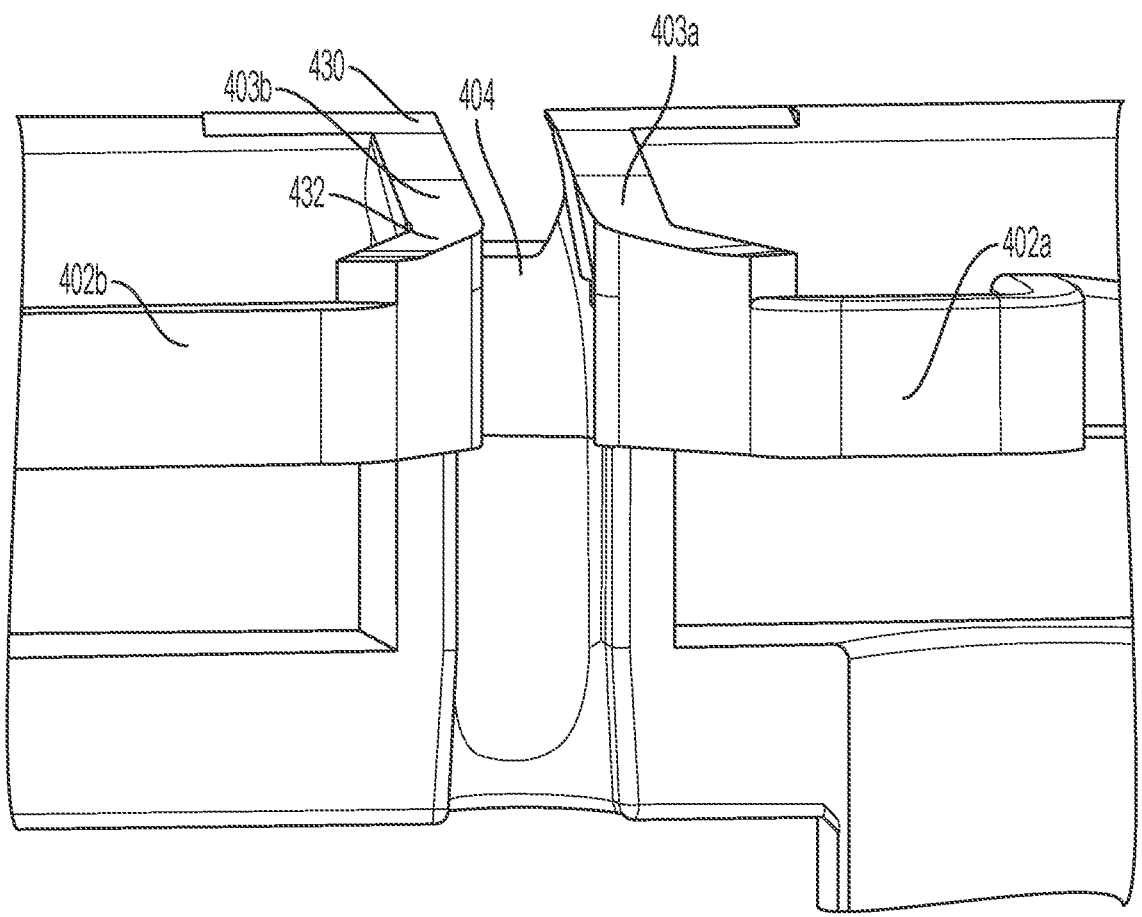
Figure 35:
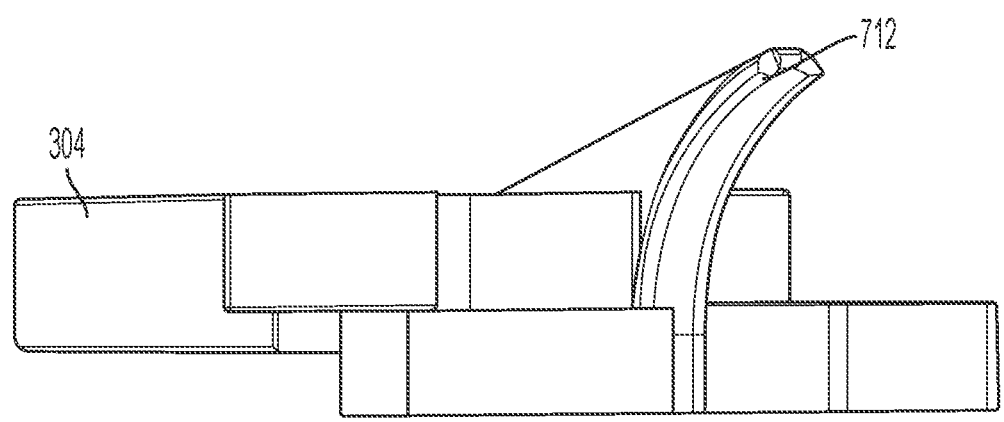

FIGS. 34 and 35 are diagrams of an embodiment where the pusher 712 is also wider and integrated into the door 304. In addition, the hood rails 403 have straight sides. When the door 304 is closed, the pusher 712 is dimensioned to fit between the hood rails 403 and retain the IV tube 304 in place. An internal face of the pusher 712 may have a surface curvature that matches a surface curvature of an IV tube to enable the pusher 712 to partially encircle the IV tube to apply force against the IV tube without causing an occlusion.

Figure 36:
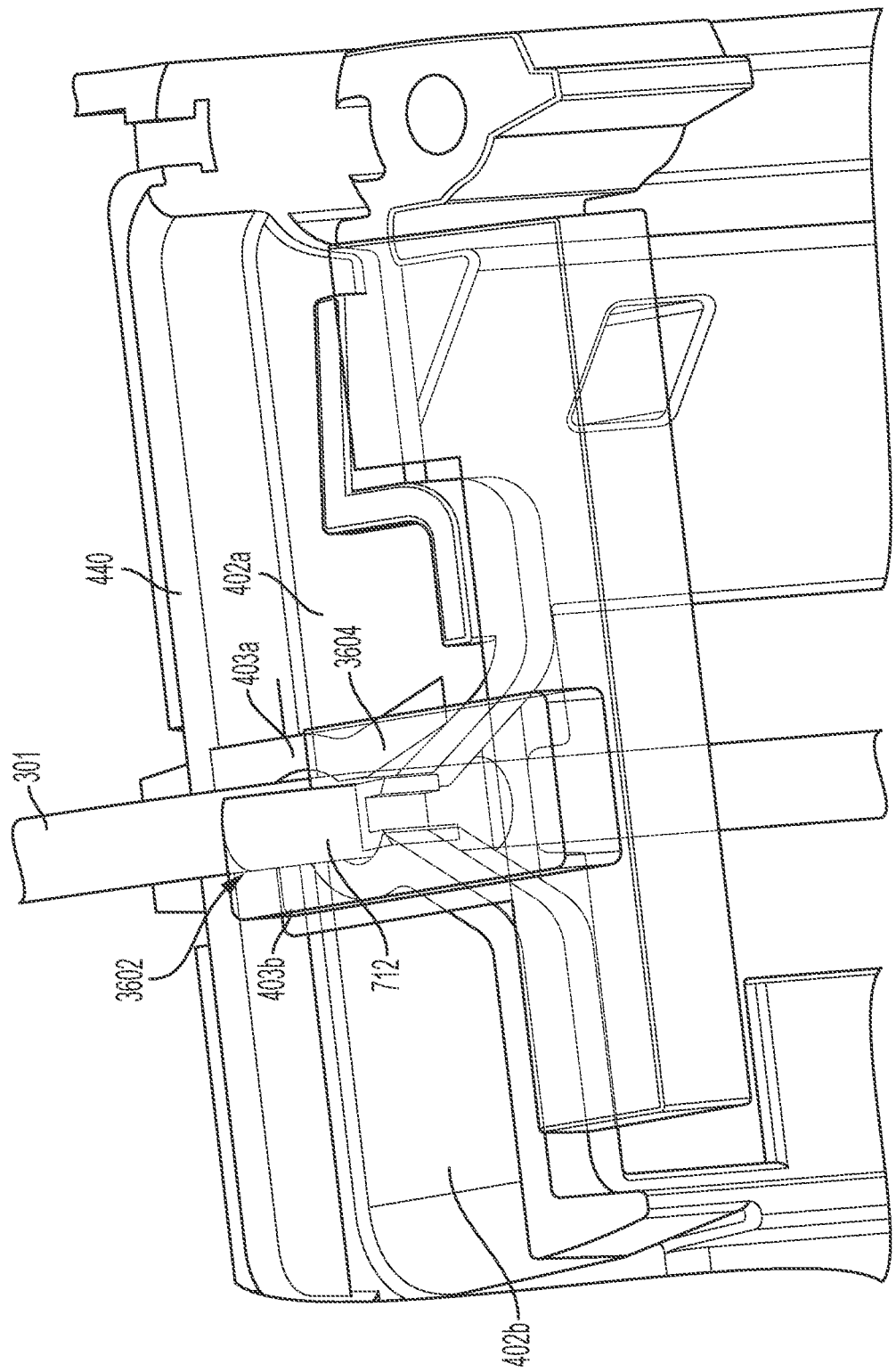
Figure 37:
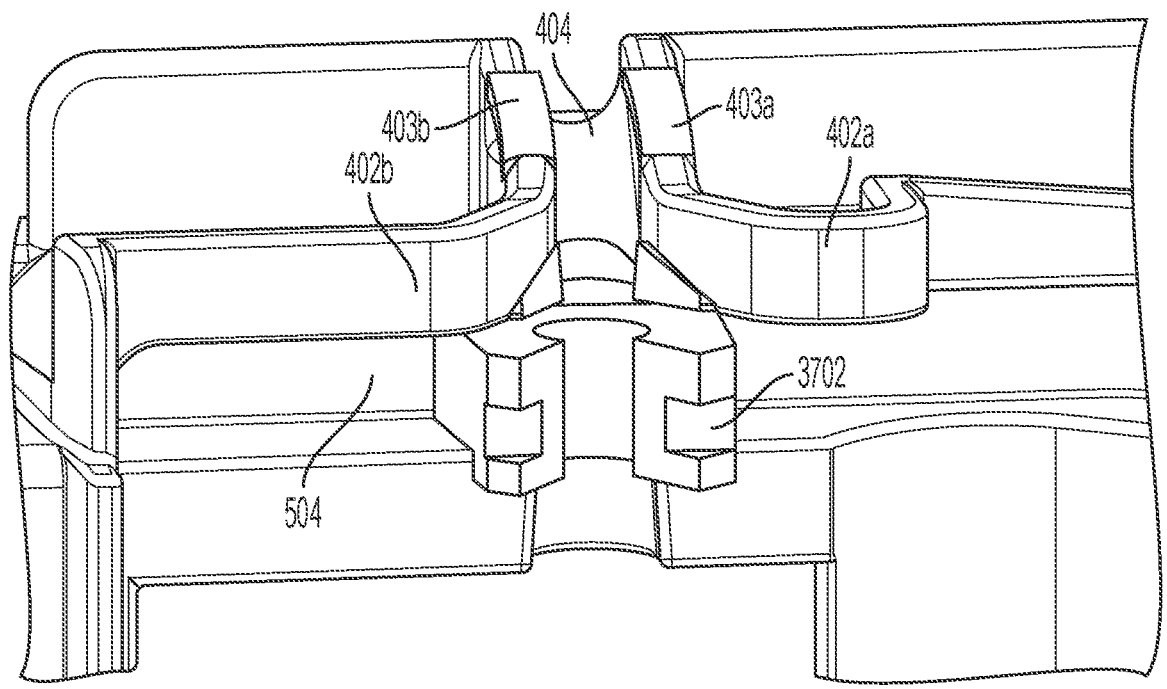

FIG. 36 is a diagram of an embodiment where the pusher 712 is formed as an integral piece that is configured to at least partially encircle ⅓ to ½ (e.g., a top side) of the IV tube 301. The pusher 712 includes a biased side 3602 configured to push the IV tube 301 in an x-direction (along a horizontal plane) for positioning within the tube channel 404. The hood rail 403b has a lower height to accommodate the biased side 3602 compared to the height of the hood rail 403a. As illustrated, the hood rail 403a contacts a non-biased side 3604 of the pusher 712 for enclosing and retaining the IV tube 301.

FIGS. 37 to 40 are diagrams of an embodiment where the hood rails 403a and 403b have raised sides configured to prevent misloading of the IV tube 301. In addition, the infusion pump 300 includes a clip 3702 located below the hood 402 within the gap 504. The clip 3702 is dimensioned to form a passage or tube channel to accommodate the IV tube 301. In addition, ends of the clip 3702 are angled inward to retain the IV tube 301 in place.

Figure 38:
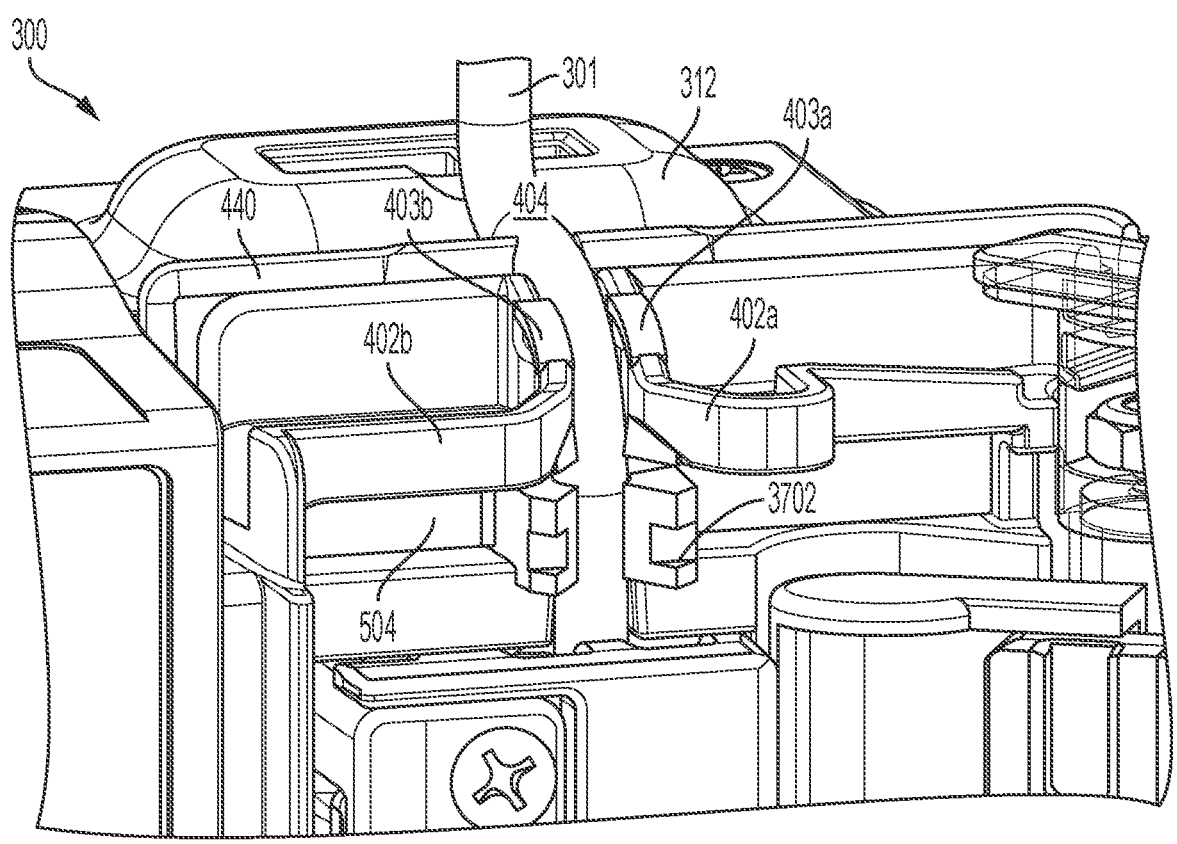

FIG. 38 shows the hood rails 403 and the clip 3702 retaining the IV tube 301. To insert the tube 301, an operator first places a first portion of the tube 301 within the hood rails 403. The curvature of a side face of the hoods 402a and 402b directs the tube 301 to the tube channel 404 between the hood rails 403 for easy alignment and placement. An operator then inserts an adjacent portion of the IV tube 301 into the clip 3702, which retains the IV tube. In some instances, an operator may be able to insert the first and second portions of the IV tube 301 at approximately the same time to easily secure the IV tube in place. In addition, the clip 3702, the hood rails 403, and the curvature of the side face of the hoods 402 provides for automatic alignment and retention of the IV tube 301 when the door 304 is moved to a closed position.

Figure 39:
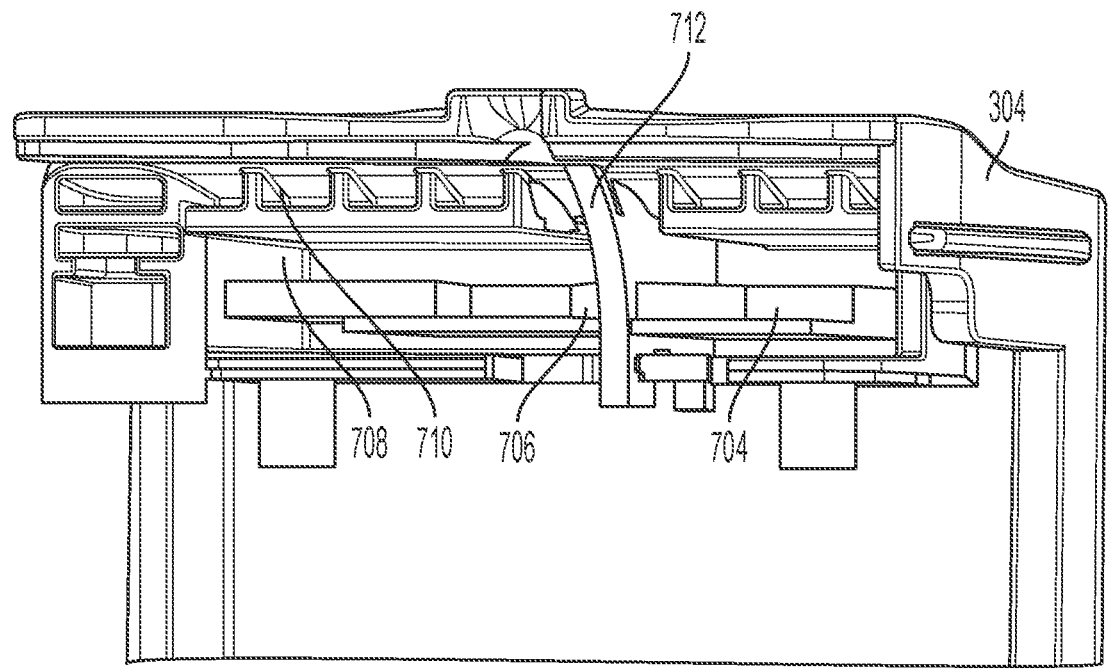
Figure 40:
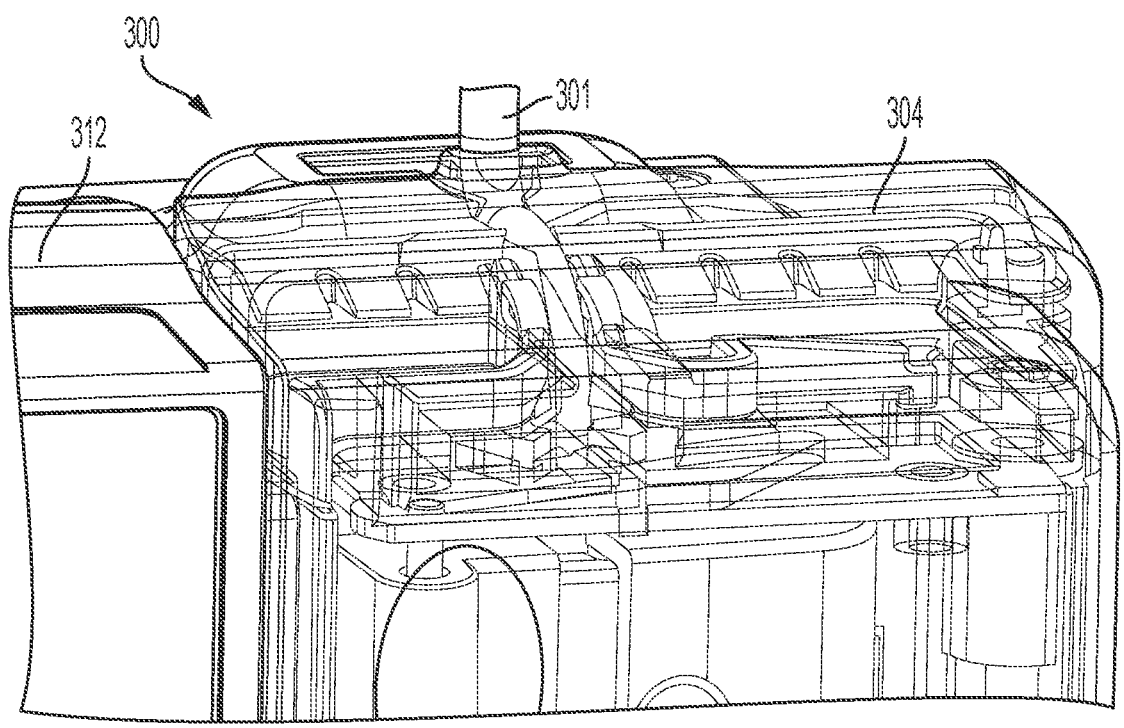

FIG. 39 is a diagram of the door 304, including self-alignment features 704, 706, 708, 710, and 712 that operate with the hood rails 403, the hoods 402a and 402b, and the clip 3702 to retain the IV tube 301. The example pusher 712 is configured to engage and/or partially enclose the IV tube at a location that is downstream from the hood rails 403 and aligned with the clip 3702. At least a portion of the pusher 3702 is configured to fit within the ends of the clip 3702, thereby securing the IV tube 301 in place. FIG. 40 is a diagram of the door 304 in the closed position with the IV tube 301 secured in place and in proper alignment to enable a fluid to pass through for an infusion therapy.

CONCLUSION

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. An infusion pump apparatus for delivering an intravenous ("IV") fluid, the apparatus comprising:
    a housing including
        an actuation area configured to engage a first portion of an IV tube in a vertical orientation when the infusion pump is positioned for operation, the actuation area including a top end for receiving the IV tube from a fluid container and a bottom end for providing the IV tube to a patient,
        a tube channel located at the top end of the actuation area, the tube channel having a surface curvature and a width configured to accept a bottom side of a second portion of the IV tube, at least a portion of the tube channel having a radial curvature for bending the second portion of the IV tube from a horizontal orientation to a vertical orientation when the infusion pump is positioned for operation,
        two parallel hood rails provided on either side of the tube channel, the hood rails having widths that extend outwardly from the tube channel, and
        a hood having a first side and a second side that are separated by the hood rails, the first and second sides connected to the hood rails; and
    a door connected to the housing and configured to enclose the actuation area, the tube channel, the hood rails, and the hood of the housing, the door including a cavity having dimensions sized to receive the hood rails and the hood when the door is in a closed position,
    wherein the hood and the hood rails are configured to engage the cavity to prevent the door from closing if the second portion of the IV tube is not positioned between the hood rails along the tube channel,
    wherein the first side of the hood includes a cutout that is located on an opposite end from an end that is connected to the respective hood rail, the cutout reducing a width of the first side of the hood at the location of the cutout, and
    wherein the first side of the hood and the cutout cooperate to cause a misaligned second portion of the IV tube to move further away from the tube channel to exaggerate the misalignment.

2. The apparatus of claim 1, wherein each of the hood rails includes a retention knob configured to retain the second portion of the IV tube within the tube channel.

3. The apparatus of claim 1, wherein the cavity includes a tab that is positioned and arranged to fit within the cutout of the first side of the hood.

4. An infusion pump apparatus for delivering an intravenous ("IV") fluid, the apparatus comprising:
    a housing including
        an actuation area configured to engage a first portion of an IV tube in a vertical orientation when the infusion pump is positioned for operation, the actuation area including a top end for receiving the IV tube from a fluid container and a bottom end for providing the IV tube to a patient,
        a tube channel located at the top end of the actuation area, the tube channel having a surface curvature and a width configured to accept a bottom side of a second portion of the IV tube, at least a portion of the tube channel having a radial curvature for bending the second portion of the IV tube from a horizontal orientation to a vertical orientation when the infusion pump is positioned for operation,
        two parallel hood rails provided on either side of the tube channel, the hood rails having widths that extend outwardly from the tube channel, and
        a hood having a first side and a second side that are separated by the hood rails, the first and second sides connected to the hood rails; and
    a door connected to the housing and configured to enclose the actuation area, the tube channel, the hood rails, and the hood of the housing, the door including a cavity having dimensions sized to receive the hood rails and the hood when the door is in a closed position,
    wherein the hood and the hood rails are configured to engage the cavity to prevent the door from closing if the second portion of the IV tube is not positioned between the hood rails along the tube channel, and
    wherein the cavity of the door is defined at least by:
        an upper-pre-alignment guide configured to contact or be adjacent to a top face of the hood; and
        a lower pre-alignment guide configured to contact or be adjacent to a bottom face of the hood.

5. The apparatus of claim 4, wherein the upper pre-alignment guide includes channels configured to engage or receive the respective hood rails.

6. The apparatus of claim 4, wherein the housing further includes:
    under-hood rails positioned adjacent to the respective hood rails and located on each side of the tube channel; and
    guide ribs positioned a distance away from the respective under-hood rails and located on each side of the tube channel for retaining the second portion of the IV tube,
    wherein gaps are formed between the under-hood rails and the guide ribs.

7. The apparatus of claim 6, wherein the lower-pre-alignment guide includes:
    cutouts configured to respectively receive the under-hood rails; and a guide section configured to be received in the gaps formed between the under-hood rails and the guide ribs, wherein a bottom face of the lower-pre-alignment guide is located so as to contact or be located adjacent to the guide ribs.

8. The apparatus of claim 7, wherein the under-hood rails, the gaps, and the guide ribs are configured to interlock or overlap with the lower-pre-alignment guide to prevent the door from closing if the second portion of the IV tube is not positioned along the tube channel.

9. The apparatus of claim 7, wherein the guide section has at least one of a u-shape or a v-shape.

10. An infusion pump apparatus for delivering an intravenous ("IV") fluid, the apparatus comprising:
a housing including
an actuation area configured to engage a first portion of an IV tube in a vertical orientation when the infusion pump is positioned for operation, the actuation area including a top end for receiving the IV tube from a fluid container and a bottom end for providing the IV tube to a patient,
a tube channel located at the top end of the actuation area, the tube channel having a surface curvature and a width configured to accept a bottom side of a second portion of the IV tube, at least a portion of the tube channel having a radial curvature for bending the second portion of the IV tube from a horizontal orientation to a vertical orientation when the infusion pump is positioned for operation,
two parallel hood rails provided on either side of the tube channel, the hood rails having widths that extend outwardly from the tube channel, and
a hood having a first side and a second side that are separated by the hood rails, the first and second sides connected to the hood rails; and
a door connected to the housing and configured to enclose the actuation area, the tube channel, the hood rails, and the hood of the housing, the door including a cavity having dimensions sized to receive the hood rails and the hood when the door is in a closed position,
wherein the hood and the hood rails are configured to engage the cavity to prevent the door from closing if the second portion of the IV tube is not positioned between the hood rails along the tube channel,
wherein the door further includes a pusher aligned with or located adjacent to the tube channel when the door is in the closed position, the pusher having a surface curvature and a width sized to accept a top side of the second portion of the IV tube, at least a portion of the pusher having a radial curvature for bending the IV tube from the horizontal orientation to the vertical orientation when the infusion pump is positioned for operation, and
wherein the width of the pusher enables the pusher to fit between the parallel hood rails when the door is in the closed position.

11. The apparatus of claim 10, wherein the housing further includes a seal section located along at least the top side of the housing, the seal section including:
at least one rib positioned along the top side of the housing, the at least one rib extending vertically from the top side and defining a tube window having a width sized to enable the second portion of the IV tube to pass between edges of the tube window; and
a rib tube channel aligned with the tube window, the rib tube channel having a horizontal orientation when the infusion pump is positioned for operation, the rib tube channel located adjacent to the tube channel and configured to contact the bottom side of the second portion of the IV tube.

12. The apparatus of claim 11, wherein the pusher in connection with the tube channel and the rib tube channel enclose or surround the bottom and top sides of the second portion of the IV tube and provide for bending the second portion of IV tube from the horizontal orientation to the vertical orientation.

13. The apparatus of claim 1, wherein the housing further includes a clip at an end of the tube channel configured to receive the second portion of the IV tube.

14. An infusion pump apparatus for delivering an intravenous ("IV") fluid, the apparatus comprising:
a housing including
an actuation area configured to engage a first portion of an IV tube in a vertical orientation when the infusion pump is positioned for operation, the actuation area including a top end for receiving the IV tube from a fluid container and a bottom end for providing the IV tube to a patient,
a housing tube channel located at the top end of the actuation area, the housing tube channel having a surface curvature and a width sized to accept a bottom side of a second portion of the IV tube, at least a portion of the housing tube channel having a radial curvature for bending the second portion of the IV tube from a horizontal orientation to a vertical orientation when the infusion pump is positioned for operation,
a first set of housing ribs located on a first side of the housing tube channel and a second set of housing ribs located on a second, opposite side of the housing tube channel; and
a door connected to the housing and configured to enclose the actuation area, the housing tube channel, and the housing ribs, the door including
a door tube channel configured to align with the housing tube channel when the door is in a closed position, and
a first set of door ribs located on a first side of the door tube channel and a second set of door ribs located on a second side of the door tube channel,
wherein the first and second sets of housing ribs are configured to interlock or overlap with the first and second sets of door ribs when the door is in the closed position.

15. The apparatus of claim 14, wherein each of the first and second sets of housing ribs includes at least three parallel ribs and each of the first and second sets of door ribs includes at least two parallel ribs.

16. The apparatus of claim 14, wherein the housing tube channel, the door tube channel, the first and second sets of housing ribs, and first and second sets of door ribs include at least one of plastic, rubber, or combinations thereof.

17. The apparatus of claim 14, wherein the door further includes an upper pre-alignment guide that is configured to contact or be adjacent to a top rib of the first and second sets of housing ribs.

18. The apparatus of claim 14, wherein the door tube channel includes a pusher having a surface curvature and a width sized to accept a top side of the second portion of the IV tube, at least a portion of the pusher having a radial curvature for bending the IV tube from the horizontal orientation to the vertical orientation when the infusion pump is positioned for operation.

19. The apparatus of claim 14, wherein the door further includes a roof configured to cover the top end of the actuation area, and wherein the door tube channel, the first set of door ribs, and the second set of door ribs are located on the roof of the door.

\* \* \* \* \*